(12) United States Patent
Akella et al.

(10) Patent No.: US 7,081,240 B1
(45) Date of Patent: Jul. 25, 2006

(54) PROTEIN MIXTURES FOR WOUND HEALING

(75) Inventors: Rama Akella, Austin, TX (US); John P. Ranieri, Austin, TX (US)

(73) Assignee: Zimmer OrthoBioLogics, Inc., Austin, TX (US)

( * ) Notice: Subject to any disclaimer, the term of this patent is extended or adjusted under 35 U.S.C. 154(b) by 0 days.

(21) Appl. No.: 09/605,266

(22) Filed: Jun. 28, 2000

(51) Int. Cl.
*A61K 45/00* (2006.01)
*A61K 35/32* (2006.01)
*C12N 5/00* (2006.01)

(52) U.S. Cl. .................. 424/85.1; 424/549; 435/372; 530/840

(58) Field of Classification Search .................. 514/12, 514/2, 55; 530/350
See application file for complete search history.

(56) References Cited

U.S. PATENT DOCUMENTS

| | | | | |
|---|---|---|---|---|
| 4,950,483 A | * | 8/1990 | Ksander et al. | |
| 5,116,738 A | | 5/1992 | Wang et al. | 435/69.1 |
| 5,141,905 A | | 8/1992 | Rosen et al. | 435/69.1 |
| 5,187,076 A | | 2/1993 | Wozney et al. | 435/69.1 |
| 5,290,763 A | * | 3/1994 | Poser et al. | |
| 5,356,630 A | | 10/1994 | Laurencin et al. | 424/426 |
| 5,371,191 A | * | 12/1994 | Poser et al. | |
| 5,393,739 A | * | 2/1995 | Bentz et al. | |
| 5,459,047 A | * | 10/1995 | Wozney et al. | |
| 5,543,394 A | * | 8/1996 | Wozney et al. | |
| 5,563,124 A | * | 10/1996 | Damien et al. | |
| 5,616,490 A | * | 4/1997 | Sullivan et al. | |
| 5,935,978 A | * | 8/1999 | Fenton et al. | 514/352 |
| 6,054,122 A | | 4/2000 | MacPhee et al. | 424/94.4 |
| 6,124,273 A | * | 9/2000 | Drohan et al. | |
| 6,150,328 A | * | 11/2000 | Wang et al. | |
| 6,177,406 B1 | * | 1/2001 | Wang et al. | 514/12 |

FOREIGN PATENT DOCUMENTS

| | | | |
|---|---|---|---|
| EP | 433225 A1 | * | 6/1991 |
| EP | 0 747 066 A2 | | 5/1996 |
| WO | 96/41818 | | 12/1996 |
| WO | 02/47713 A | | 5/2002 |

OTHER PUBLICATIONS

Stedman's Medical Dictionary, copyright © 2002 by Medical Economics Company, Inc. at Montvale, NJ 07645.*
Stelincki et al. Plastic and Resonstructive Surgery, 1998, vol. 101, pp. 12-19.*
American Heritage® Dictionary of the English Language (Fourth Edition 2000 by Houghton Mifflin Company—"derived".*
The American Heritage® Dictionary of the English Language, 2000.*
International Search Report dated Jan. 29, 2003 for International application No. PCT/US01/41110 Filed Jun. 22, 2001.

* cited by examiner

*Primary Examiner*—Brenda Brumback
*Assistant Examiner*—Cherie M. Woodward
(74) *Attorney, Agent, or Firm*—Williams, Morgan & Amerson, P.C.

(57) ABSTRACT

A protein mixture that is useful in the treatment of wounds, where the mixture is isolated from bone or is produced from recombinant proteins and may include two or more of BMP-2, BMP-3, BMP-4, BMP-5, BMP-6, BMP-7, TGF-β1, TGF-β2, TGF-β3, and FGF-1.

19 Claims, 39 Drawing Sheets

| BAND NO. | IDENTITY |
|---|---|
| 1 | HISTONE H1.c |
| 2 | HISTONE H1.c |
| 3 | RIBOSOMAL PROTEIN RS20 |
| 4 | SIMILAR TO RIBOSOMAL PROTEIN LORP |
| 5 | BMP-3 |
| 6 | α2 MACROGLOBULIN RAP AND BMP-3 |
| 7 | SIMILAR TO RIBOSOMAL PROTEIN LORP |
| 8 | BMP-3 |
| 9 | BMP-3 |
| 11 | RIBOSOMAL PROTEIN RL6 AND BMP-3 |
| 18 | TGF-β2/SPP 24 |
| 20 | FACTOR H |
| 22 | TGF-β2 |
| 25 | BMP-3 AND H1.x |
| 29 | BMP-3 AND RIBOSOMAL PROTEIN RL32 |

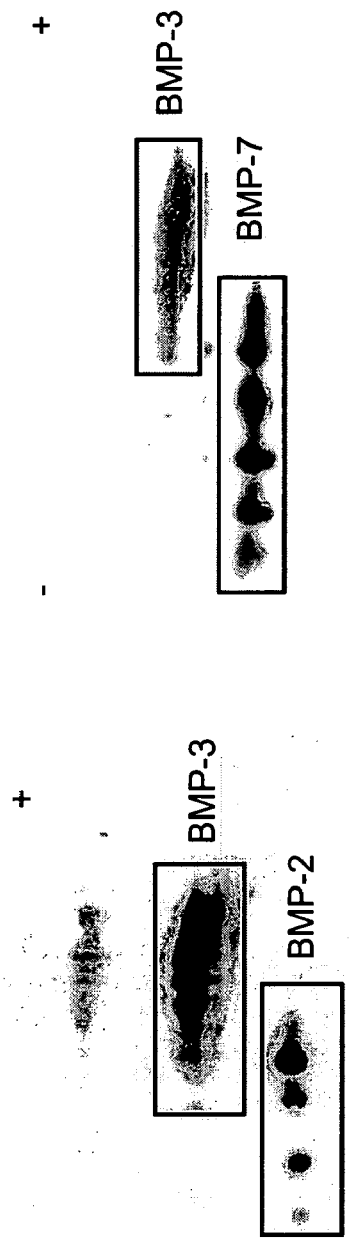
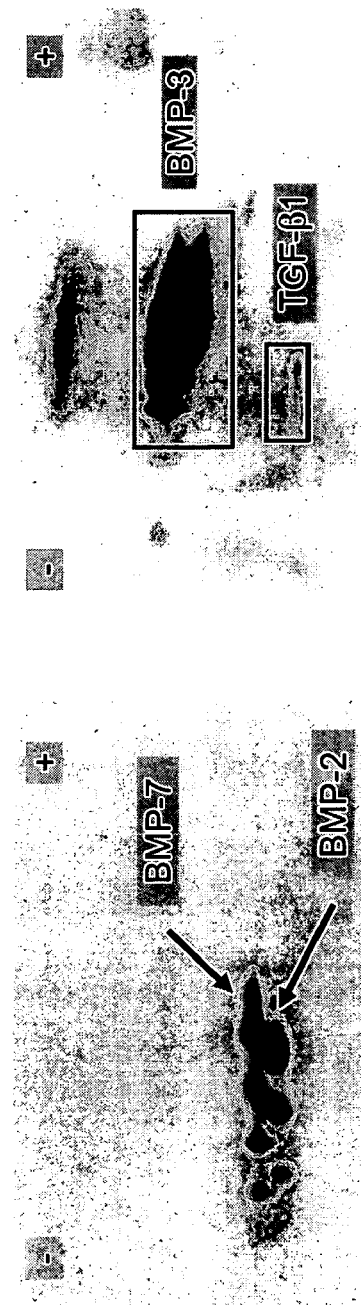
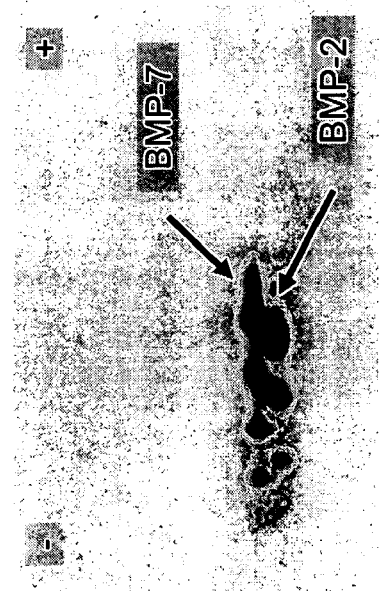
FIG. 9A  FIG. 9B  FIG. 9C  FIG. 9D

ANTIBODY LISTING

| SPECIFICITY | ANTIGEN | HOST SPECIES | PC/MC | SOURCE | CATALOG NO. |
|---|---|---|---|---|---|
| TGF-$\beta$1(HUMAN) | PROTEIN | RABBIT | POLYCLONAL | PROMEGA | G1221 |
| TGF-$\beta$2(HUMAN) | PEPTIDE | RABBIT | POLYCLONAL | SANTA CRUZ BIOTECHNOLOGY | sc-90 |
| TGF-$\beta$3(HUMAN) | PEPTIDE | RABBIT | POLYCLONAL | SANTA CRUZ BIOTECHNOLOGY | sc-82 |
|  |  |  |  |  |  |
| BMP-2 (HUMAN) | PROTEIN | RABBIT | POLYCLONAL | AUSTRAL BIOLOGICS | PA-513-9 |
| BMP-3 (HUMAN) | PEPTIDE | CHICKEN | POLYCLONAL | RESEARCH GENETICS | NA |
| BMP-4 (HUMAN) | PEPTIDE | GOAT | POLYCLONAL | SANTA CRUZ BIOTECHNOLOGY | so-6896 |
| BMP-5 (HUMAN) | PEPTIDE | GOAT | POLYCLONAL | SANTA CRUZ BIOTECHNOLOGY | sc-7405 |
| BMP-6 (HUMAN) | PEPTIDE | MOUSE | MONOCLONAL | NOVOCASTRA LABORATORIES | NCL-BMP6 |
| BMP-7 (HUMAN) | PEPTIDE | RABBIT | POLYCLONAL | RESEARCH GENETICS | NA |
|  |  |  |  |  |  |
| FGF-1 (HUMAN) | PEPTIDE | GOAT | POLYCLONAL | SANTA CRUZ BIOTECHNOLOGY | sc-1884 |
| OSTEONECTIN (BOVINE) | PROTEIN | MOUSE | MONOCLONAL | DSHB | AON-1 |
| OSTEONECTIN (BOVINE) | PROTEIN | RABBIT | POLYCLONAL | ACCURATE CHEMICALS | A761/R1H |
| SERUM ALBUMIN (BOVINE) | PROTEIN | RABBIT | POLYCLONAL | CHEMICON INTERNATIONAL | AB870 |
| TRANSFERRIN (HUMAN) | PROTEIN | CHICKEN | POLYCLONAL | CHEMICON INTERNATIONAL | AB797 |
| apo-A1 LIPOPROTEIN (HUMAN) | PROTEIN | GOAT | POLYCLONAL | CHEMICON INTERNATIONAL | AB740 |

FIG.14

IDENTIFICATION OF PROTEINS BY AMINO ACID SEQUENCING OF TRYPTIC FRAGMENTS FROM 1D GELS

| BAND | SAMPLE | SEQUENCE DATA | BEST DATABASE MATCH | MATCH | IDENTIFICATION | SPECIES | ACC. NO. | AAs | SEQ ID NO: |
|---|---|---|---|---|---|---|---|---|---|
| 1 | | | | | | | | | |
| 2 | fx 49 (1579) | XLAAAGYDVEK | ALAAAGYDVEK | 11/11 | HISTONE H1.c | HUMAN | 87668 (NCBI) | 65-75 | 1 |
| 3 | fx 67 (1346) | SLEKVCADLIR | SLEKVCADLIR | 11/11 | 40s RIBOSOMAL PROTEIN S20 | RAT | R3R120 (PIR) | 31-41 | 2 |
| 4 | fx 55 0 | (V)VCGMLGFPSEAPV | VVCGMLGFPGEKRV | 11/14 | LORP | MOUSE | AAC95338 (NCBI) | 213-226 | 3 |
| 5 | N TERMINAL seq | STGVLLPLQNNELPG | STGVLLPLQNNELPG | 15/15 | BMP-3 | HUMAN | 4557371 (NCBI) | 290-304 | 4 |
| | fx 72 (3925) | STGVLLPLQNNELPGAEYQY | STGVLLPLQNNELPGAEYQY | 20/20 | BMP-3 | HUMAN | 4557371 (NCBI) | 290-304 | 5 |
| | fx 74 (3409) | STGVLLPLQ | STGVLLPLQ | 9/9 | BMP-3 | HUMAN | 4557371 (NCBI) | 290-298 | 6 |
| 6 | fx 55 (1566) | (S)QTLQFXE | SQTLQFDE | 7/8 | BMP-3 | HUMAN | 4557371 (NCBI) | 346-353 | 7 |
| | fx 47 | VYAF | NO MATCH | | ??? | | | | 8 |
| | N TERMINAL SEQ | HAGKYSREKNT(P)A(P) | HGGKYSREKNQPKP | 11/14 | α2-MACROGLOBULIN RECEPTOR ASSOC. PRO. | HUMAN | P30533 (SWISS-PROT) | 31-46 | 9 |
| | fx 57 (1438) | SQTLQFDEQ | SQTLQFDEQ | 9/9 | BMP-3 | HUMAN | 4557371 (NCBI) | 346-354 | 10 |
| | fx 57 (1652) | SLKPSNHA | SLKPSNHA | 8/8 | BMP-3 | HUMAN | 4557371 (NCBI) | 410-417 | 11 |
| 7 | fx 51 (1093) | AALRPLVKP | AALRPLVKP | 9/9 | 60s RIBOSOMAL PROTEIN L32 | MOUSE | P17932 (SWISS-PROT) | 1-9 | |
| | fx 37 (NO MS) | A(H)I(Q)VERYV | AIVER | 5/5 | 60s RIBOSOMAL PROTEIN L32 | MOUSE | P17932 (SWISS-PROT) | 109-113 | 12 |
| | fx 37 (NO MS) | A(H)I(Q)VERYV | HQSDRYV | 5/7 | 60s RIBOSOMAL PROTEIN L32 | MOUSE | P17932 (SWISS-PROT) | 22-28 | 12 |
| 8 | fx 78 () | XALF(G)AQLGXALGPI | NO MATCH | | ??? | | | | 13 |
| 9 | fx 56 (1567) | SQTLQFDEQT | SQTLQFDEQT | 10/10 | BMP-3 | HUMAN | P12645 (SWISS-PROT) | 346-355 | 14 |

FIG.15A

IDENTIFICATION OF PROTEINS BY AMINO ACID SEQUENCING OF TRYPTIC FRAGMENTS FROM 1D GELS

| BAND | SAMPLE | SEQUENCE DATA | BEST DATABASE MATCH | MATCH | IDENTIFICATION | SPECIES | ACC. NO. | AAs | SEQ ID NO: |
|---|---|---|---|---|---|---|---|---|---|
| 11 | fx 55 (1311) | SQTLXF | SQTLQF | 5/6 | BMP-3 | HUMAN | 4557371 (NCBI) | 346–351 | 15 |
|  | fx 47 (1772) | VLATVTKPVGGDK | VLATVTKPVGGDK | 13/13 | 60s RIBOSOMAL PROTEIN L6 | HUMAN | Q02878 (SWISS-PROT) | 87–99 | 16 |
|  | fx 76 (1795) | xVFAL | VFAL | 4/4 | 60s RIBOSOMAL PROTEIN L6 | HUMAN | Q02878 (SWISS-PROT) | 273–276 | 17 |
|  | fx 61 (1145) | AVPQLQGYLR | AIPQLQGYLR | 9/10 | 60s RIBOSOMAL PROTEIN L6 | HUMAN | Q02878 (SWISS-PROT) | 262–271 | 18 |
| 18 |  |  |  |  |  |  |  |  |  |
| 22 | fx 69 (1145) | ALDAAYCFR | ALDAAYCFR | 9/9 | TGF-β2 | HUMAN | P08112 (SWISS-PROT) | 303–311 | 19 |
|  | fx 58 (NO MATCH) | GYNANFCAGACPYL | GYNANFCAGACPYL | 14/14 | TGF-β2 | HUMAN | P08112 (SWISS-PROT) | 340–353 | 20 |
|  | fx 66 (1411.71) | VNSQSLSPY | VNSQSLSPY | 9/9 | SPP24 | BOVINE | Q27967 (SWISS-PROT) | 42–50 | 21 |
| 25 | fx 39 (1470) | KAAKPSV(P) | KAAKPSVP | 8/8 | HISTONE H1.x | HUMAN | JC4928 (PIR) | 199–206 | 22 |
| 29 |  |  |  |  |  |  |  |  |  | fx = FRACTION NUMBER (MOLECULAR WEIGHT OF FRAGMENT, AS MEASURED BY SDS-PAGE)

FIG. 15B

IDENTIFICATION OF PROTEINS BY MASS SPECTROMETRY OF TRYPTIC FRAGMENTS FROM 1D GELS

| BAND | MASS SPEC PROFILE | SPECIES | ACC. NO. | MASS SPEC DATA | MASS SPEC DATABASE | MASS DIFFERENCE | AAs | % COVERAGE | COMMENTS |
|---|---|---|---|---|---|---|---|---|---|
| 1 | 4 PEAKS MATCH WITH HISTONE H1.c | HUMAN | 87668 (NCBI) | 1172.97 | 1172.37 | 0.60 | 110-121 | 22 | 15 MS PEAKS MATCH WITH BAND 2 |
|  |  |  |  | 1579.87 | 1579.71 | 0.16 | 65-79 |  |  |
|  |  |  |  | 1708.47 | 1707.89 | 0.58 | 64-79 |  |  |
|  |  |  |  | 2011.58 | 2012.32 | -0.74 | 35-54 |  |  |
| 2 | 3 PEAKS MATCH WITH HISTONE H1.c | HUMAN | 87668 (NCBI) | 1579.76 | 1579.71 | 0.05 | 65-79* | 16 | IDENTIFICATION OF STARRED PEPTIDE CONFIRMED BY SEQUENCE ANALYSIS |
|  |  |  |  | 1708.02 | 1707.89 | 0.13 | 64-79 |  | 15 MS PEAKS MATCH WITH BAND 1 |
|  |  |  |  | 2012.12 | 2012.32 | -0.20 | 35-54 |  |  |
| 3 | 7 PEAKS MATCH WITH RIBOSOME S20 | RAT | R3RT20 PIR | 1129.76 | 1129.40 | 0.36 | 50-59 | 62 |  |
|  |  |  |  | 1156.21 | 1156.30 | -0.09 | 76-83 |  |  |
|  |  |  |  | 1334.46 | 1334.62 | -0.16 | 56-66 |  |  |
|  |  |  |  | 1352.13 | 1351.58 | 0.55 | 88-99 |  |  |
|  |  |  |  | 1518.04 | 1517.77 | 0.27 | 9-21 |  |  |
|  |  |  |  | 1919.02 | 1919.19 | -0.17 | 5-21 |  |  |
|  |  |  |  | 3404.02 | 3404.87 | -0.85 | 88-119 |  |  |
| 4 | 3 PEAKS MATCH WITH LYSYL OXIDASE RP | HUMAN | NP002309 (SWISS-PROT) | 1987.95 | 1988.27 | -0.32 | 150-167 | 8 | 12 MS PEAKS MATCH WITH BAND 8 |
|  |  |  |  | 2410.35 | 2410.63 | -0.28 | 648-669 |  |  |
|  |  |  |  | 2610.57 | 2610.10 | 0.47 | 455-478 |  |  |

FIG.16A

IDENTIFICATION OF PROTEINS BY MASS SPECTROMETRY OF TRYPTIC FRAGMENTS

| BAND | MASS SPEC PROFILE | SPECIES | ACC. NO. | MASS SPEC DATA | MASS SPEC DATABASE | MASS DIFFERENCE | AAs | % COVERAGE | COMMENTS |
|---|---|---|---|---|---|---|---|---|---|
| 5 | 9 PEAKS MATCH WITH BMP-3 | HUMAN | 4557371 (NCBI) | 1113.32 | 1113.31 | 0.01 | 361-368 | 48 | % COVERAGE CALCULATION IS RELATIVE TO THE MATURE BMP-3, 183 AAS (290-472) |
| | | | | 1438.53 | 1438.58 | -0.05 | 346-357 | | |
| | | | | 1566.76 | 1566.76 | 0.00 | 345-357 | | |
| | | | | 1651.86 | 1651.91 | -0.05 | 410-424 | | |
| | | | | 1794.09 | 1794.02 | 0.07 | 346-360 | | |
| | | | | 2268.46 | 2268.63 | -0.17 | 374-392 | | |
| | | | | 2424.45 | 2424.81 | -0.36 | 373-392 | | IDENTIFICATION OF STARRED PEPTIDE CONFIRMED BY SEQUENCE ANALYSIS |
| | | | | 3409.15 | 3407.77 | 1.38 | 290-318* | | |
| 6 | 3 PEAKS MATCH WITH α2-MACROGLOBULIn RAP | HUMAN | P30533 (SWISS-PROT) | 1002.24 | 1002.15 | 0.09 | 283-290 | 17 | |
| | | | | 2362.58 | 2362.43 | 0.15 | 129-150 | | |
| | | | | 3048.51 | 3048.52 | -0.01 | 257-282 | | |
| | 2 PEAKS MATCH WITH BMPS-3 | HUMAN | 4557371 (NCBI) | 1566.93 | 1566.75 | 0.18 | 346-357 | 15 | % COVERAGE CALCULATION IS RELATIVE TO THE MATURE BMP-3, 183 AAS (290-472) |
| | | | | 1651.88 | 1651.91 | -0.03 | 410-424 | | |

FIG.16B

IDENTIFICATION OF PROTEINS BY MASS SPECTROMETRY OF TRYPTIC FRAGMENTS FROM 1D GELS

| BAND | MASS SPEC PROFILE | SPECIES | ACC. NO. | MASS SPEC DATA | MASS SPEC DATABASE | MASS DIFFERENCE | AAs | % COVERAGE | COMMENTS |
|---|---|---|---|---|---|---|---|---|---|
| 7 | 4 PEAKS MATCH WITH RIBOSOME L32 | MOUSE | P17932 (SWISS-PROT) | 1033.25 | 1033.17 | 0.08 | 67-75 | 33 | |
| | 5 PEAKS MATCH WITH BMP-3 | HUMAN | 4557371 (NCBI) | 1093.31 | 1093.40 | -0.09 | 1-10* | 21 | % COVERAGE CALCULATION IS RELATIVE TO THE MATURE BMP-3, 183 AAS (290-472) |
| | | | | 1134.72 | 1134.28 | 0.44 | 65-74 | | |
| | | | | 1449.78 | 1449.66 | 0.12 | 19-29 | | |
| | | | | 1060.42 | 1060.20 | 0.22 | 102-111 | | |
| 8 | 1 PEAK MATCHES WITH LYSYL OXIDASE RP | HUMAN | NP002309 (SWISS-PROT) | 1113.39 | 1113.31 | 0.08 | 361-368 | 3 | 12 MS PEAKS MATCH WITH BAND 4 |
| | | | | 1360.26 | 1360.58 | -0.32 | 190-200 | | |
| | | | | 1652.28 | 1651.91 | 0.37 | 410-424 | | |
| | | | | 1793.62 | 1794.02 | -0.40 | 346-360 | | |
| | | | | 2410.37 | 2410.63 | -0.26 | 648-669 | | |
| 9 | 6 PEAKS MATCH WITH BMP-3 | HUMAN | 4557371 (NCBI) | 1113.14 | 1113.31 | -0.17 | 361-368 | 36 | % COVERAGE CALCULATION IS RELATIVE TO THE MATURE BMP-3, 183 AAS (290-472) |
| | | | | 1438.60 | 1438.58 | 0.02 | 346-357 | | |
| | | | | 1566.77 | 1566.76 | 0.01 | 345-357 | | |
| | | | | 1651.91 | 1651.61 | 0.30 | 410-424 | | |
| | | | | 2901.67 | 2901.19 | 0.48 | 41-66 | | |
| | | | | 3408.94 | 3407.77 | 1.17 | 290-318 | | |

FIG. 16C

IDENTIFICATION OF PROTEINS BY MASS SPECTROMETRY OF TRYPTIC FRAGMENTS FROM 1D GELS

| BAND | MASS SPEC PROFILE | SPECIES | ACC. NO. | MASS SPEC DATA | MASS SPEC DATABASE | MASS DIFFERENCE | AAs | % COVERAGE | COMMENTS |
|---|---|---|---|---|---|---|---|---|---|
| 11 | 5 PEAKS MATCH WITH BMP-3 | MOUSE | 4557371 (NCBI) | 1113.23 | 1113.31 | -0.08 | 361-368 | 48 | % COVERAGE CALCULATION IS RELATIVE TO THE MATURE BMP-3, 183 AAS (290-472) |
| | | | | 1651.73 | 1651.91 | -0.18 | 410-424 | | |
| | | | | 1793.58 | 1794.02 | -0.44 | 346-360 | | |
| | | | | 2424.24 | 2424.81 | -0.57 | 373-392 | | |
| | | | | 3408.34 | 3407.77 | 0.57 | 290-318 | | |
| | 5 PEAKS MATCH WITH RIBOSOME L6 | HUMAN | Q02878 (SWISS-PROT) | 1140.38 | 1140.23 | 0.15 | 114-122 | 16 | |
| | | MOUSE | P47911 (SWISS-PROT) | 1526.88 | 1526.86 | 0.02 | 141-155 | | |
| | | | | 1059.15 | 1059.12 | 0.03 | 10-20 | | |
| 18 | 4 PEAKS MATCH WITH TGF-β2 | HUMAN | P08112 (SWISS-PROT) | 1145.36 | 1145.35 | 0.01 | 262-271 | 52 | |
| | | | | 1386.74 | 1386.68 | 0.06 | 260-271 | | |
| | | | | 1101.20 | 1101.26 | -0.06 | 303-311 | | |
| | | | | 1175.26 | 1175.42 | -0.16 | 400-409 | | |
| | | | | 2240.37 | 2240.60 | -0.23 | 312-328 | | |
| | | | | 2691.70 | 2691.91 | -0.21 | 340-362 | | |
| | 5 PEAKS MATCH WITH SPP24 | BOVINE | Q27967 (SWISS-PROT) | 1410.93 | 1411.60 | -0.67 | 42-53 | 30 | |
| | | | | 1447.59 | 1477.65 | -0.06 | 113-124 | | |
| | | | | 1540.64 | 1540.60 | 0.04 | 86-98 | | |
| | | | | 1869.10 | 1869.05 | 0.05 | 62-77 | | |
| | | | | 2268.47 | 2268.57 | -0.10 | 33-53 | | |

FIG. 16D

IDENTIFICATION OF PROTEINS BY MASS SPECTROMETRY OF TRYPTIC FRAGMENTS FROM 1D GELS

| BAND | MASS SPEC PROFILE | SPECIES | ACC. NO. | MASS SPEC DATA | MASS SPEC DATABASE | MASS DIFFERENCE | AAs | % COVERAGE | COMMENTS |
|---|---|---|---|---|---|---|---|---|---|
| 22 | 5 PEAKS MATCH WITH TGF-β2 | HUMAN | P08112 (SWISS-PROT) | 1101.15 | 1101.26 | -0.11 | 303-311 | 48 | |
| | | | | 1175.13 | 1175.42 | -0.29 | 400-409 | | |
| | | | | 2084.16 | 2084.42 | -0.26 | 312-347 | | |
| | | | | 2240.25 | 2240.60 | -0.35 | 312-328 | | |
| | | | | 2691.61 | 2891.91 | -0.30 | 340-362 | | |
| | 2 PEAKS MATCH WITH SPP24 | BOVINE | Q27967 (SWISS-PROT) | 1411.23 | 1411.60 | -0.37 | 42-53 | 11 | |
| | | | | 1447.40 | 1447.65 | -0.25 | 113-124 | | |
| | 5 PEAKS MATCH WITH HISTONE H1.x | HUMAN | JC4928 (SWISS-PROT) | 1208.46 | 1208.40 | 0.06 | 48-57 | 14 | |
| | | | | 1221.71 | 1222.35 | -0.64 | 107-118 | | |
| | | | | 1349.85 | 1350.52 | -0.67 | 107-119 | | |
| | | | | 1364.57 | 1364.59 | -0.02 | 48-58 | | |
| | | | | 1732.23 | 1732.97 | -0.74 | 43-57 | | |
| 25 | 5 PEAKS MATCH WITH BMP-3 | HUMAN | 4557371 (NCBI) | 1060.43 | 1060.20 | 0.23 | 102-111 | 31 | % COVERAGE CALCULATION IS RELATIVE TO THE MATURE BMP-3, 183 AAS (290-472) |
| | | | | 1438.83 | 1438.58 | 0.25 | 346-357 | | |
| | | | | 1566.92 | 1566.76 | 0.16 | 345-357 | | |
| | | | | 1651.80 | 1651.91 | -0.11 | 410-424 | | |
| | | | | 3408.86 | 3407.77 | 1.09 | 290-318 | | |

FIG.16E

IDENTIFICATION OF PROTEINS BY MASS SPECTROMETRY OF TRYPTIC FRAGMENTS FROM 1D GELS

| BAND | MASS SPEC PROFILE | SPECIES | ACC. NO. | MASS SPEC DATA | MASS SPEC DATABASE | MASS DIFFERENCE | AAs | % COVERAGE | COMMENTS |
|---|---|---|---|---|---|---|---|---|---|
| 29 | 4 PEAKS MATCH WITH BMP-3 | HUMAN | 4557371 (NCBI) | 1113.22 | 1113.31 | -0.09 | 361-368 | 27 | % COVERAGE CALCULATION IS RELATIVE TO THE MATURE BMP-3, 183 AAS (290-472) |
| | | | | 1438.70 | 1438.58 | 0.12 | 346-357 | | |
| | | | | 1566.86 | 1566.75 | 0.11 | 345-357 | | |
| | | | | 3409.04 | 3407.77 | 1.27 | 290-318 | | |

FIG.16F

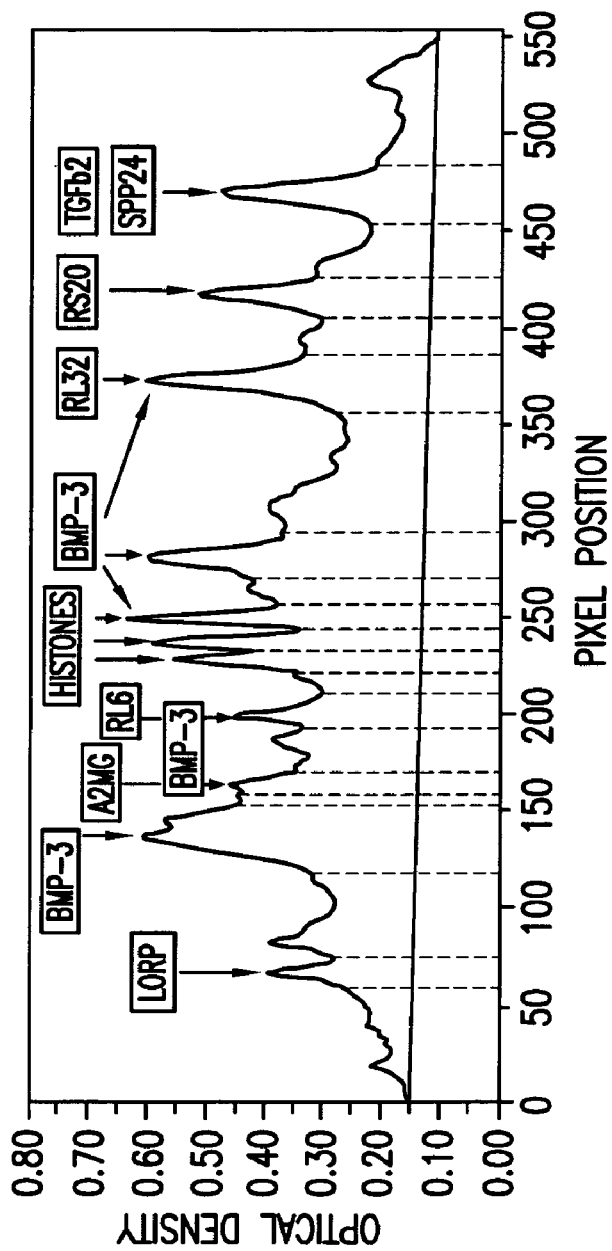
FIG. 17A
FIG. 17B

QUANTITATION OF IDENTIFIED BP PROTEINS

| IDENTIFIED PROTEIN | PERCENTAGE OF TOTAL PROTEIN |
|---|---|
| LORP | 2 |
| BMP-3 | 11 |
| BMP-3 AND A2-MG | 3 |
| RL6 & BMP-3 | 4 |
| HISTONE | 3 |
| HISTONE | 3 |
| HISTONE & BMP-3 | 4 |
| BMP-3 | 8 |
| RL32 & BMP-3 | 8 |
| RS2D | 5 |
| SPP24 & TGF-$\beta$2 | 6 |
| TOTAL | 58% |

FIG.18

IDENTIFICATION OF PROTEINS BY MASS SPECTROMETRY OF FRAGMENTS FROM 2D GELS

| BAND | DIGEST | MASS SPEC PROFILE | SPECIES | ACC. NO. | MS PEAKS DATA | MS PEAKS DATABASE | DIFF | AAs | % COVERAGE | COMMENTS |
|---|---|---|---|---|---|---|---|---|---|---|
| 1 | Lys-C | 2 PEAKS MATCH WITH COAGULATION FACTOR XIIIb | HUMAN | P05160 (SWISS-PROT) | 1837.01 | 1837.14 | -0.13 | 472-487 | 8 | |
| | | | | | 1921.65 | 1921.14 | 0.51 | 366-382 | | PEPTIDE MATCH CONFIRMED BY SEQUENCE ANALYSIS |
| | | | | | 2679.51 | N/A | N/A | 488-504 | | |
| 2 | TRYPSIN | 2 PEAKS MATCH WITH LORP | HUMAN | NP002309 (SWISS-PROT) | 1609.57 | 1609.88 | -0.31 | 241-253 | 5 | |
| | | | | | 2410.89 | 2410.63 | 0.26 | 648-669 | | |
| 3 | Lys-C | 8 PEAKS MATCH WITH CATHEPSIN L PRECURSOR | BOVINE | P25975 (SWISS-PROT) | 1407.26 | 1406.80 | 0.46 | 105-116 | 41 | |
| | | | | | 1546.84 | 1546.70 | 0.14 | 58-70 | | |
| | | | | | 1661.16 | 1660.80 | 0.36 | 21-33 | | |
| | | | | | 1681.86 | 1680.80 | 1.06 | 301-314 | | |
| | | | | | 1834.71 | 1834.00 | 0.71 | 318-334 | | |
| | | | | | 2352.90 | 2351.50 | 1.40 | 274-295 | | |
| | | | | | 2381.50 | 2380.70 | 0.80 | 239-261 | | |
| | | | | | 2721.51 | 2721.10 | 0.41 | 131-154 | | |

FIG. 19A

IDENTIFICATION OF PROTEINS BY MASS SPECTROMETRY OF FRAGMENTS FROM 2D GELS

| SPOT | DIGEST | MASS SPEC PROFILE | SPECIES | ACC. NO. | MS PEAKS DATA | MS PEAKS DATABASE | DIFF | AAs | % COVERAGE | COMMENTS |
|---|---|---|---|---|---|---|---|---|---|---|
| 4 | Lys-C | 2 PEAKS MATCH WITH LYSYL OXIDASE | RAT | P16636 (SWISS-PROT) | 1461.58 | N/A | N/A | | | PEPTIDE MATCHES CONFIRMED BY SEQUENCE ANALYSIS |
| | | | | | 4595.08 | 4593.06 | 2.02 | | | |
| 5 | Lys-C | 3 PEAKS MATCH WITH TGF-b2 | BOVINE | P21214 (SWISS-PROT) | 774.56 | 774.90 | -0.34 | 26-31 | 20 | |
| | | | | | 809.67 | 809.94 | -0.27 | 32-37 | | |
| | | | | | 1175.26 | 1175.43 | -0.17 | 98-107 | | |
| | | 2 PEAKS MATCH WITH SPP24 | BOVINE | Q27967 (SWISS-PROT) | 1415.56 | 1415.58 | -0.02 | 42-60 | 16 | |
| | | | | | 2187.98 | 2187.51 | 0.47 | 21-32 | | |
| 2 | TRYPSIN | 13 PEAKS MATCH WITH SPP24 | BOVINE | Q27967 (SWISS-PROT) | 1078.06 | 1078.15 | -0.09 | 78-85 | 60 | |
| | | | | | 1101.07 | 1101.31 | -0.24 | 99-108 | | |
| | | | | | 1172.42 | 1172.31 | 0.11 | 99-108 | | |
| | | | | | 1411.53 | 1411.60 | -0.07 | 42-53 | | |
| | | | | | 1447.63 | 1447.65 | -0.02 | 113-124 | | |
| | | | | | 1540.57 | 1540.52 | 0.05 | 86-98 | | |
| | | | | | 1696.79 | 1696.71 | 0.08 | 85-98 | | |
| | | | | | 1869.16 | 1869.05 | 0.11 | 62-77 | | |
| | | | | | 2026.01 | 2025.24 | 0.77 | 61-77 | | |
| | | | | | 2272.97 | 2272.56 | 0.41 | 21-41 | | |
| | | | | | 2600.18 | 2599.65 | 0.53 | 78-98 | | |
| | | | | | 2693.30 | 2693.81 | -0.51 | 86-108 | | |
| | | | | | 2928.80 | 2928.01 | 0.79 | 125-151 | | |

FIG. 19B

IDENTIFICATION OF PROTEINS BY MASS SPECTROMETRY OF FRAGMENTS FROM 2D GELS

| SPOT | DIGEST | MASS SPEC PROFILE | SPECIES | ACC. NO. | MS PEAKS DATA | DATABASE | DIFF | AAs | % COVERAGE | COMMENTS |
|---|---|---|---|---|---|---|---|---|---|---|
| 7 | Lys-C | 4 PEAKS MATCH WITH TGF-b2 | BOVINE | P21214 (SWISS-PROT) | 774.56 | 774.90 | -0.34 | 26-31 | 42 | |
| | | | | | 809.69 | 809.94 | -0.25 | 32-37 | | |
| | | | | | 1175.12 | 1175.43 | -0.31 | 98-107 | | |
| | | | | | 3168.10 | 3166.66 | 1.44 | 1-25 | | |
| | | 1 PEAK MATCHES WITH SPP24 | BOVINE | Q27967 (SWISS-PROT) | 2187.77 | 2187.51 | 0.26 | 42-60 | 10 | |
| 8 | TRYPSIN | 12 PEAKS MATCH RIBOSOME L3 | BOVINE | P39872 (SWISS-PROT) | 917.39 | 917.14 | 0.25 | 348-355 | 37 | |
| | | | | | 984.23 | 984.15 | 0.08 | 10-18 | | |
| | | | | | 1192.62 | 1192.40 | 0.22 | 286-296 | | |
| | | | | | 1380.67 | 1380.65 | 0.02 | 249-260 | | |
| | | | | | 1464.80 | 1464.63 | 0.17 | 103-114 | | |
| | | | | | 1620.86 | 1620.82 | 0.04 | 103-115 | | |
| | | | | | 1778.84 | 1779.00 | -0.16 | 34-49 | | |
| | | | | | 2238.43 | 2238.55 | -0.12 | 30-49 | | |
| | | | | | 2325.99 | 2325.65 | 0.34 | 177-197 | | |
| | | | | | 2661.31 | 2661.04 | 0.27 | 200-223 | | |
| | | | | | 2897.94 | 2898.43 | -0.49 | 70-98 | | |
| | | | | | 2946.10 | 2946.35 | -0.25 | 198-223 | | |

FIG. 19C

IDENTIFICATION OF PROTEINS BY MASS SPECTROMETRY OF FRAGMENTS FROM 2D GELS

| SPOT | DIGEST | MASS SPEC PROFILE | SPECIES | ACC. NO. | MS PEAKS DATA | DATABASE | DIFF | AAs | % COVERAGE | COMMENTS |
|---|---|---|---|---|---|---|---|---|---|---|
| 9 | TRYPSIN | 7 PEAKS MATCH WITH RIBOSOME S3a | MOUSE | P97351 (SWISS-PROT) | 920.05 | 920.10 | -0.05 | 19-26 | 29 | |
| | | | | | 1218.29 | 1218.31 | -0.02 | 152-161 | | |
| | | | | | 1346.62 | 1346.49 | 0.13 | 151-161 | | |
| | | | | | 1516.69 | 1516.69 | 0.00 | 174-186 | | |
| | | | | | 1593.72 | 1593.82 | -0.10 | 94-106 | | |
| | | | | | 1719.91 | 1720.00 | -0.09 | 199-212 | | |
| | | | | | 1953.12 | 1953.16 | -0.04 | 65-81 | | |
| 10 | TRYPSIN | 4 PEAKS MATCH WITH HISTONE H1.c | HUMAN | 87668 (NCBI) | 1327.75 | 1327.56 | 0.19 | 34-46 | 23 | |
| | | | | | 1579.70 | 1579.71 | -0.01 | 65-79 | | |
| | | | | | 1707.65 | 1707.89 | -0.24 | 64-79 | | |
| | | | | | 2147.17 | 2147.53 | -0.36 | 1-21 | | |
| 11 | TRYPSIN | 6 PEAKS MATCH WITH RIBOSOME S4 | HUMAN | P12750 (SWISS-PROT) | 1168.48 | 1168.38 | 0.10 | 230-239 | 23 | |
| | | | | | 1216.39 | 1216.39 | 0.00 | 134-144 | | |
| | | | | | 1354.03 | 1353.61 | 0.42 | 230-241 | | |
| | | | | | 1507.81 | 1507.89 | 0.12 | 198-210 | | |
| | | | | | 1557.75 | 1557.98 | -0.23 | 37-48 | | |
| | | | | | 2140.34 | 2140.58 | -0.24 | 221-239 | | |
| | | | | | 2591.80 | 2591.90 | -0.10 | 77-99 | | |

FIG. 19D

PROTEIN MIXTURES FOR WOUND HEALING

FIELD OF THE INVENTION

The invention relates to use of protein mixtures, comprising a variety of growth factors, for use in the treatment of wounds.

BACKGROUND OF THE INVENTION

Wound healing is a complex process involving several cell types and growth factors for an effective closure. The normal wound healing process can be broadly classified into three stages namely the inflammatory, proliferative and maturation phases. The inflammatory phase lasts 0–2 days and involves an orderly recruitment of cells to the wound area. This is followed by the 2–6 day proliferative phase, in which fibroblasts, keratinocytes and other cells in the wound bed begin to actively proliferate to close the wound. The maturation phase follows the proliferative phase, peaking at 21 days, by which time the wound is completely healed by restructuring the initial scar tissue.

A problematic wound does not follow the normal time table for the healing process as described above. A problematic wound could fail to follow the normal healing process for any number of reasons, including nutrition, vascular status, metabolic factors, age, immune status, drug therapy, neurologic status and psychologic status, among others. Several local factors also play an important role in wound healing, including the presence of necrotic tissue in the area, infection, foreign body presence, degree of desiccation, presence of edema, pressure, friction, shear maceration and dermatitis.

It has been shown from wound fluid composition studies that growth factors play an important role in all three phases of wound healing. The cell types that are recruited to the wound area secrete growth factors that assist in and promote the wound healing process. Platelets, for example, are the first cell type to be recruited at the wound site, and initiate the wound healing process by secreting growth factors (i.e., platelet derived growth factors, or PDGF) which are chemotactic for other cell types. By so doing, the platelets assist in the recruitment and proliferation of additional cell types that promote synthesis of new tissue. In addition to the above mentioned functional properties, growth factors also have the ability to regulate protein synthesis within the cell and control intracellular signaling thus allowing cells to communicate with one another.

Since wound healing is a complex process which involves formation of connective tissue, and new blood vessels to nourish the site, it is evident that several growth factors come into play. In chronic wounds there is an increase in collagenase activity and higher levels of inflammatory cytokines. Additionally, there is an absence of growth factors in the wound fluid which causes the cells to be mitotically incompetent. All of these factors cause impaired wound healing. Some of these factors have been studied in the preclinical animal models as well as in the clinic. Most growth factor studies involving the wound healing process involve tests in the 20–25 day range, which appears to adequately model the normal wound healing process. However, it is now realized that to get 100% closure of problematic wounds, longer study periods such as long as 6 months or more would be advantageous.

The only FDA approved growth factor for wound healing use in the clinic is platelet derived growth factor (PDGF) marketed by Ortho-McNeil Pharmacuetical as REGRANEX®. REGRANEX® contains becaplermin, a recombinant human platelet-derived growth factor (rhPDGF-BB) for topical administration. Becaplermin is produced by recombinant DNA technology by insertion of the gene for the B chain of platelet derived growth factor (PDGF) into yeast. Becaplermin has a molecular weight of approximately 25 KD and is a homodimer composed of two identical polypeptide chains that are bound together by disulfide bonds. REGRANEX® is a non-sterile, low bioburden, preserved, sodium carboxymethylcellulose-based (CMC) topical gel, containing the active ingredient becaplermin and the inactive ingredients sodium chloride, sodium acetate trihydrate, glacial acetic acid, water for injection, and methylparaben, propylparaben, and m-cresol as preservatives and l-lysine hydrochloride as a stabilizer.

Studies of various growth factors in the wound healing process have been conducted. Some of the findings from these studies are summarized below:

1) PDGF-BB (the growth factor in REGRANEX®) is a chemoattractant for neutrophils, monocytes, and fibroblasts. In wound healing applications it has been shown to increase extracellular matrix deposition and enhance proliferation of fibroblasts. PDFG is not an angiogen, however. Thus, additional growth factors will be required for the healthy maintenance of neodermis.

2) Fibroblast Growth Factor (FGF) increases capillary density and proliferation of fibroblasts. A topical application in gel form was tested and it was shown that there was no systemic absorption of the protein (<1% of the dose detected).

3) Transforming growth factor $\beta$-2 (TGF $\beta$-2) is a growth factor that enhances proliferation of several cell types both in vitro and in vivo and has been tested in venous ulcer healing and in diabetic foot ulcer trials. In a two arm clinical study a 40% reduction of wound size compared to the control wound was observed in 6 weeks when used at 0.5 $\mu$g/cm2. However, in a 3 arm clinical study when 2.5 $\mu$g/cm2 was tested for comparison against standard XEROFORM® dressing, the results were not very encouraging.

4) Epidermal growth Factor (EGF) produced by platelets and macrophages is a mitogen for epithelial cells. This growth factor was first tested in burn patients and the initial results were promising. However, when tested in volunteers there was no difference between growth factor treatments and placebo. This could be due to the fact that EGF is not good for migration of keratinocytes, but is a good mitotic agent.

5) Keratinocyte Growth Factor-2 (KGF-2) was tested for its ability to increase ephithelialization. By day 6 the interstices were closed. KGF-2 promotes re-epithelialization in young and old animals suggesting indirect mechanisms for neo-granulation tissue formation. Xia Y. D., et al., J. Pathol. (1999) 188: 431–438. There is increased resistance to mechanical stress of healed wounds, hence KGF-2 may be useful for the treatment of surgical wounds. Jiminez, P. A. & Rampy, M. A., (1999) J. Surg. Res. 81: 238–242.

6) Connective tissue growth factor (CTGF) is a secreted, mitogenic, chemotactic and cell matrix inducing factor encoded by an immediate early growth responsive gene. Involvement of CTGF in human atherosclerosis and fibrotic disorders suggests a role in tissue regeneration like wound repair, but also in aberrant deposition of extracellular matrix. In fact, anti-CTFG antibodies have been used to block the fibrotic cascade.

Studies on the kinetics of action of various growth factors demonstrated that some growth factors such as granulocyte-monocyte colony stimulating factor (GMCSF) and bovine FGF acted sequentially. It was hypothesized that a combination of growth factors would be better than a single growth factor treatment. However, in animal models, a combination of these two factors actually slowed the regenerative process and healing never achieved 100%. Hence, sequential delivery of these factors was attempted: GMCSF was administered first followed by FGF delivery 25 days later. In a single study, no improvement over control could be demonstrated.

In yet another study combining TGF-β, bFGF (basic FGF) and CTGF it was found that TGF-β1, TGF-β2 or TGF-β3 caused skin fibrosis after 3 days of continuous injection but the change was transient and disappeared after 7 days of continuous injection. In contrast, irreversible fibrosis was observed upon simultaneous injection of TGF-β and bFGF or TGF-β and CTGF, or TGF-β injection for the first 3 days followed by bFGF or CTGF injection for the next 4 days. These observations suggest that TGF-β1 induces skin fibrosis and bFGF or CTGF maintains it in various skin fibrotic disorders.

Another way of obtaining growth factor mixtures considered the use of platelet releasate which contains a collection of growth factors released from platelets derived from blood. The advantages of this material are that it is autologous or homologous, and is readily available and presumably contains the required factors in the proper ratio. To date, although some improvement in the healing process was observed initially, by 24 weeks there was no difference between growth factor and placebo treatments.

It is thus apparent that although several polypeptide growth factors have shown significant biological activity in pre-clinical wound repair models, the only growth factor that has proven to be effective in the clinic is the human recombinant PDGF-BB. This may be due to poor delivery, drug instability or the inability of a single factor to orchestrate the complex process of wound healing. An effective treatment should address issues such as angiogenesis, efficient collagen deposition and proper epithelialization to close the wound.

SUMMARY OF THE INVENTION

The invention comprises compositions and methods for improving the wound healing process in living animals, including human subjects. In preferred embodiments, the invention comprises a mixture of growth factors which improve the wound healing process. In this context, the terms "excluding," "exclusion," or "excluded" refers to the removal of substantially all of an indicated component, to the extent that such component can be removed from a mixture with immunoaffinity chromatography or otherwise not included in the mixture. The term "pharmaceutically acceptable carrier" is used herein in the ordinary sense of the term and includes all known carriers including water.

"BP" is a protein cocktail derived from bone as described in U.S. Pat. Nos. 5,290,763, 5,371,191, and 5,563,124 (each of which is hereby incorporated by reference herein in its entirety). In brief, the cocktail is prepared by guanidine hydrochloride protein extraction of demineralized bone particles. The extract solution is filtered, and subjected to a two step ultrafiltration process. In the first ultrafiltration step an ultrafiltration membrane having a nominal molecular weight cut off (MWCO) of 100 kD is employed. The retentate is discarded and the filtrate is subjected to a second ultrafiltration step using an ultrafiltration membrane having a nominal MWCO of about 10 kD. The retentate is then subjected to diafiltration to substitute urea for guanidine. The protein-containing urea solution is then subjected to sequential ion exchange chromatography, first anion exchange chromatography followed by cation exchange chromatography. The osteoinductive proteins produced by the above process are then subjected to HPLC with a preparative VYDAC™ column at and eluted with shallow increasing gradient of acetonitrile. One minute fractions of the HPLC column eluate are pooled to make the BP cocktail (fraction number can vary slightly with solvent composition, resin size, volume of production lot, etc.). One embodiment of the BP cocktail is characterized as shown in FIGS. 1–6. Absolute and relative amounts of the growth factors present in the BP cocktail can be varied by collecting different fractions of the HPLC eluate. In a particularly preferred embodiment, fractions 29–34 are pooled. It is also contemplated that certain proteins may be excluded from the BP mixture without affecting wound healing activity.

BP was originally discovered as a mixture of proteins known to have osteogenic activity. However, it contains a plurality of growth factors and is strongly angiogenic. In particular, BP contains a number of bone morphogenetic proteins (BMPs), including BMP-2, BMP-3, BMP-4, BMP-5, BMP-6, and BMP-7, as well as TGF-β1, TGF-β2, and TGF-β3. FGF-1 is also present in the mixture. The presence of each of the foregoing proteins was detected using immunoblot techniques, as depicted FIG. 14. When BP was tested in an animal model to determine if it would be effective in aiding wound closure, it was surprisingly discovered that BP promotes wound healing, even though it is a markedly different process than osteogenesis.

The protein compositions of the invention can be advantageously combined with traditional wound dressings including primary and secondary dressings, wet-to-dry dressings, absorbent dressings, nonadherent dressings, semipermeable dressings, transparent dressings, hydrocolloid dressings, hydrogels, foam dressings, alginate dressings, surgical tapes and the like as is appropriate for the type of wound being treated.

Compositions according to the present invention may also be combined with a variety of other active ingredients, such as aloe vera, arginine, glutamine, zinc, copper, vitamin C, B vitamins and other nutritional supplements, antibiotics, antiseptics, antifungals, deodorizers, and the like. Embodiments of the invention can also be combined with a variety of anti-inflammatory agents that inhibit the action of proinflammatory cytokines such as interleukin-1, interleukin-6 and tumor necrosis factor-alpha. Many such inhibitors are well known, such as IL-1Ra, soluble TGF-β receptor, cortocosteroids, and it is believed that more will be discovered in the future.

In one embodiment, the invention is a composition for the treatment of wounds comprising the proteins BMP-3 and TGF-β2 in a pharmaceutically acceptable carrier. As shown in FIG. 18, BMP-3 is the growth factor present in the highest concentration in the BP mixture. TGF-β2 is believed to play an important role in wound healing because it promotes the proliferation of several cell types, which is important, for example, in the proliferative stage of the wound healing process. As already noted, TGF-β2 alone has been the subject of study as a wound healing agent. Without limitation as to specific mechanisms, it is believed that these two growth factors may be significant in the wound healing activity displayed by BP.

In another embodiment, compositions of the present invention comprise BMP-3, TGF-β2, and one or more of BMP-2, BMP-4, BMP-5, BMP-6, and BMP-7 in a pharmaceutically acceptable carrier. BMP-6 is known to induce a cascade of events leading to the expression of both BMP-2 and BMP-4, both of which are known to have osteogenic activity. BMP-2 has also been implicated in the regulation of kidney tissue regeneration. BMP-7 (also known as OP-1) is currently undergoing preclinical testing as a wound healing agent.

In still another embodiment, compositions of the present invention comprise BMP-3, TGF-$\beta$2, one or more of BMP-2, BMP-4, BMP-5, BMP-6, and BMP-7, and one or more of FGF-1, TGF-$\beta$1, and TGF-$\beta$3. FGF-1 is known to be an angiogenic growth factor, although its activity is not as pronounced as FGF-2, which has not been detected in BP. TGF-$\beta$1 and TGF-$\beta$3 are both known to enhance cell proliferation.

The presence of a number of proteins which are believed to have no growth factor activity has been detected in BP. Accordingly, these proteins, including histone proteins, ribosomal proteins, or both, may be excluded from compositions of the present invention. Alternatively, the composition may comprise the BP mixture isolated as described in U.S. Pat. Nos. 5,290,763, 5,371,191, and 5,563,124 as shown in FIGS. 2 and 3 (lanes inside the box pooled to make BP). Histones and ribosomes may be excluded from the BP by, for example, antibody binding or other techniques known in the art. Additionally, the composition of matter may contain one or more of the listed active components supplied as a recombinantly produced protein. Preferably, the components are isolated from a natural source and are at least partially phosphorylated and glycosylated.

In another embodiment, the above compositions are used in wound healing applications together with a pharmaceutically acceptable carrier. The pharmaceutically acceptable carrier includes dressings such as hydrocolloid dressings, hydrogels, foam dressings, and alginate dressings. Additional active ingredients may include arginine, glutamine, zinc, copper, vitamin C, vitamin B1, vitamin B2, vitamin B3, vitamin B6, vitamin B12, and folate or growth factors such as epidermal growth factor, platelet derived growth factor, insulin-like growth factor, keratinocyte growth factor, vascular endothelial growth factor, transforming growth factor alpha, nerve growth factor, connective tissue growth factor and granulocyte-monocyte colony stimulating factor. Inflammation inhibitor, such as interleukin-1 inhibitor, interleukin-6 inhibitor and tumor necrosis factor-alpha inhibitor may also be added to the composition. Of course, pain relief agents, disinfectants, antibiotics and other active ingredients suitable for particular wound applications may also be added thereto.

DESCRIPTION OF THE DRAWINGS

FIGS. 9A–D are 2-D gel Western blots of a protein mixture according to an embodiment of the present invention, labeled with indicated antibodies. FIG. 9A indicates the presence of BMP-3 and BMP-2. FIG. 9B indicates the presence of BMP-3 and BMP-7. FIG. 9C indicates the presence of BMP-7 and BMP-2, and FIG. 9D indicates the presence of BMP-3 and TGF-$\beta$1.

FIG. 14 is a chart showing antibody listing and reactivity.

FIGS. 15A–B together comprise a chart showing tryptic fragment sequencing data for components of a protein mixture according to an embodiment of the present invention.

FIGS. 16A–F together comprise a chart showing tryptic fragment mass spectrometry data for components of a protein mixture according to an embodiment of the present invention.

FIGS. 17A–B are an SDS-gel (FIG. 17B) and a scanning densitometer scan (FIG. 17A) of the same gel for a protein mixture according to an embodiment of the present invention.

FIG. 18 is a chart illustrating the relative mass, from scanning densitometer quantification, of protein components in a protein mixture according to an embodiment of the present invention.

FIGS. 19A–D together comprise a chart showing mass spectrometry data of various protein fragments from 2D gels of a protein mixture according to an embodiment of the present invention.

DETAILED DESCRIPTION OF THE INVENTION

Example 1

Figure 1:
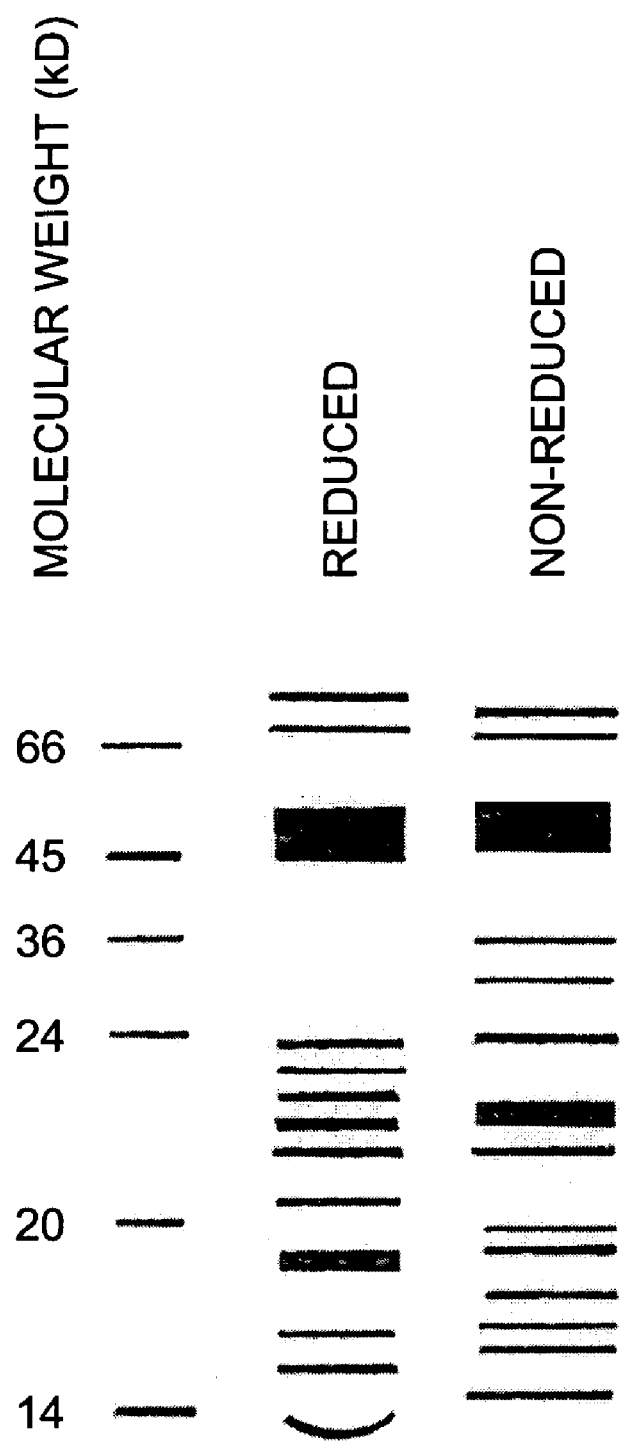
FIG. 1 illustrates an SDS-PAGE of a protein mixture according to the present invention, both in reduced and nonreduced forms.

BP in Single Dose Application to Nude Mice

A single dose application of BP to full thickness wounds in nude mice covered with human meshed split thickness skin grafts has been found to heal the wound completely and faster than wounds not receiving the growth factor mixture. Although the specific manner in which the growth factors in BP affect the wound healing process is not fully understood, it is hypothesized that the synergistic action of the multiple growth factors present in BP helps the wounds recover better than those in control animals that have received the carrier alone.

Full thickness wounds were created in nude mice such that the wound area comprised about 20% of the total body surface. BP was prepared as in U.S. Pat. Nos. 5,290,763, 5,371,191, and 5,563,124, and applied to the wound in a povidone carrier. The wound was then covered with human meshed split thickness skin grafts. The control group of animals received only the povidone carrier. The graft sites were dressed and closed with band-aids to keep the dressing securely in place. The first dressing changes were carried out on day 5 post operative and every third day thereafter. The basic protocol is also described in "Clinical and Experimental Approaches to Dermal and Epidermal Repair: Normal and Chronic Wounds," pp. 429–442 (1991) Wiley-Liss, Inc. and Cooper M. L., et al., The Effects of Epidermal Growth factor and basic Fibroblast Growth factor on Epithelialization of Meshed Skin Graft Interstices, Prog. Clin. Biol. Res. (1991) 365: 429–42. Such protocols are known to persons of skill in the art.

The results were strongly encouraging. Single application of two concentrations (either 100 µg/wound site or 200 µg/wound site) of growth factor were tested. There was no difference either in the rate or degree of wound healing between the two groups. However, there was a marked difference between the group of animals that received the growth factor treatment and the control animals that did not receive the growth factor. By day 11 POD (post operative day), a 95% wound closure was observed in the animals that received the growth factor whereas the control animals showed only a 74% closure. By day 14 POD all growth factor treated animals had a 100% closure while the control animals had only a 85% closure as of day 20 POD.

The thickness of the epithelial layer in BP treated wounds was significantly higher in BP treated animals compared to the control animals, as shown in Table 1. The data represents the thickness of neodermis in mm measured on day 11 for the BP treated animals and day 16 for the control animals such that measurements are made at equivalent extents of healing. Histological analysis revealed that the wounds were closed by the human cells from the grafted material and there was collagen deposition in the closed wounds as revealed by involucrin and collagen type 1 immuno histological staining (data not shown). The capillary density in the wound bed following BP treatment was also significantly higher at the time of wound closure compared to untreated controls, as shown in Table 1. Further, in the animals treated with the lower BP dosage, there was a significant increase in the smooth muscle cell (SMC) count in the BP treated wounds as compared to the controls, as also seen in Table 1.

In summary, a single dose application of BP was effective in reducing the healing time of full thickness wound in nude mice grafted with human meshed split thickness skin. Additionally, the thickness of the neodermis and the density of the capillaries in the treated wounds were significantly higher compared to the control group of animals. In contrast, bFGF, also an angiogenic growth factor, was shown to have a deleterious effect on epithelialization when tested in a similar animal model. (Cooper, M. L. et al., 1991; Clinical and experimental approaches to dermal and epidermal repair: normal and chronic wounds, pp 429–442; Weilly-Liss, Inc.).

Example 2

BP in Hydrogel

A small number of animals (n=3) were treated with BP solubilized in a hydrogel (carboxy-methyl cellulose) in the same animal model as described above. In this study, it was observed that the wounds (n=2) treated with BP in the hydrogel showed initiation of epithelialization as early as 5 days post operation compared to the wounds treated with BP solubilized in 1% povidone which showed initiation of epithelialization only at 8 days post operation (data not shown). In both instances, the control animals that received the carrier alone did not show initiation of epithelialization until POD 8. Detailed histology is being carried out on the tissue samples to determine the thickness of the neodermis and the degree of angiogenesis in the wounds treated with the hydrogel formulation. However, wound closure data is presented in Table 2, below.

TABLE 2

Percent Wound Closure for BP and Control Treated Wounds.

| | | Percent Wound Closure (%) | | | |
|---|---|---|---|---|---|
| | Animal # | POD 5 | POD 8 | POD 11 | POD 14 |
| *Control (no BP) | 1 | 0 | 50 | 70 | 70 |
| Control (hydrogel, no BP, no salts) | 2 | 25 | 70 | 70 | 100 |
| BP & hydrogel, no salts | 3 | 0 | 70 | 90 | 100 |
| BP & hydrogel, no salts | 4 | 25 | 80 | 90 | 90 |
| BP & hydrogel, salts (some precipitate formed, probably due to buffering salts) | 5 | 0 | 80 | 90 | 100 |

*The control animal had very thin and fragile skin at the time of biopsy compared to the animals which received BP.

In summary, the results were very promising although preliminary, showing quicker wound closure in BP treated than control animals. Thus, more extensive experiments were undertaken to confirm the results, as described below.

TABLE 1

Wound Thickness, Capillary Count and SMC Count for BP and Control Treated Wounds.

| | Treatment | | |
|---|---|---|---|
| | 100 µg BP (n = 5) | 200 µg BP (n = 5) | Control (n = 10) |
| Epithelial Thickness (mm) | 1.60 ± 0.12 ($P < 0.001$) | 1.55 ± 0.09 ($P < 0.001$) | 1.1 ± 0.25 |
| Capillary/Field | 37 ± 6 ($P < 0.01$) | 35 ± 7 ($P < 0.01$) | 25 ± 5.9 |
| SMC counts/Field | 53 ± 3.5 ($P < 0.001$) | 46.8 ± 4.4 ($P < 0.05$) | 46 ± 5.8 |

Example 3

Compapative Study Between REGRENEX® and BP

REGRANEX® (PDGF-BB), the only approved growth factor product in the market for treating diabetic foot ulcers, showed complete healing in 50% of the patient population compared to the 35% placebo gel treatment that demonstrated complete healing after repeat application for about 20 weeks in diabetic patients (see REGRANEX® U.S. full prescribing information—package insert). Hence, a comparison of REGRANEX(r) (tm) versus BP was undertaken in a study similar to that described above. The results are presented in Tables 3 and 4.

TABLE 3

BP, Hydrogel (HG) and Regranex ® Treated Wounds and Percent Wound Closure (%), Epithelial Thickness (mm) and Degree of Angiogenesis (# Estimated Capillaries per 20× Field).

| Animal # | Treatment Group | Percent (%) Wound Closure | | | | Epi. Thick. (μm) | Angio. (# est. cap/hpf 20×) |
|---|---|---|---|---|---|---|---|
| | | POD 5 | POD 8 | POD 11 | POD 14 | POD 14 | POD 14 |
| 1 | BP | 10 | 25 | 85 | 100 | 17.5 | 28 |
| 2 | BP | 10 | | | | | |
| 3 | BP | 15 | | | | | |
| 4 | BP | 10 | | | | | |
| 5 | BP | 10 | 30 | 85 | 80 | 7.5 | 16 |
| 6 | BP | 10 | | | | | |
| 7 | BP | 10 | 10 | | | | |
| 8 | BP | 10 | 30 | 85 | 100 | 11.5 | 26 |
| 9 | BP | 30 | 50 | 85 | 100 | 16 | 21 |
| 10 | BP | 30 | 50 | 85 | 100 | 12 | 20 |
| 11 | BP | 20 | 45 | 85 | 100 | 18 | 18 |
| 12 | BP | 10 | 15 | 85 | 90 | 6 | 20 |
| 13 | BP | 10 | 20 | 95 | 100 | 5.5 | 23 |
| 14 | BP | 15 | 25 | 90 | 100 | 10 | 32 |
| 15 | BP | 5 | 50 | 90 | 95 | 14 | 25 |
| n | | 15 | 11 | 10 | 10 | 10 | 10 |
| mean | | 13.67 | 31.82 | 87.00 | 96.50 | 11.80 | 22.9 |
| SD | | 7.43 | 14.71 | 3.50 | 6.69 | 4.58 | 4.88 |
| SEM | | 0.54 | 0.46 | 0.04 | 0.07 | 0.39 | |
| 16 | HG | 15 | 35 | 75 | 55 | 12.5 | 28 |
| 17 | HG | 10 | 60 | 70 | 95 | 10.5 | 5 |
| 18 | HG | 5 | 25 | 60 | 95 | 9 | 34 |
| 19 | HG | 10 | 30 | 70 | 90 | 17.5 | 8 |
| 20 | HG | 20 | 40 | 80 | 95 | 17.5 | 20 |
| 21 | HG | 10 | 10 | 80 | 95 | 13 | 15 |
| 22 | HG | 30 | 80 | 70 | 90 | 10 | |
| 23 | HG | 10 | 80 | 80 | 90 | 20 | 10 |
| 24 | HG | 15 | 40 | 70 | 90 | 18 | 15 |
| 25 | HG | 20 | 35 | 70 | 90 | 10.5 | 16 |
| 26 | HG | 10 | 10 | 70 | 90 | 12.5 | 20 |
| 27 | HG | 10 | 35 | 70 | 90 | 8 | 32 |
| 28 | HG | 10 | 55 | | | | |
| 29 | HG | 5 | 40 | | | | |
| 30 | HG | 15 | 40 | 70 | | | |
| n | | 15 | 15 | 13 | 12 | 12 | 11 |
| mean | | 13.00 | 41.00 | 71.92 | 88.75 | 13.25 | 18.455 |
| SD | | 6.49 | 20.72 | 5.60 | 10.90 | 4.01 | 9.55 |
| SEM | | 0.50 | 0.51 | 0.08 | 0.12 | 0.30 | |
| 31 | Regranex | 20 | 30 | 55 | 75 | 16 | |
| 32 | Regranex | 15 | 80 | | | | 13 |
| 33 | Regranex | 20 | 80 | 100 | 100 | 8.5 | 4 |
| 34 | Regranex | 15 | 50 | 90 | 100 | 10 | |
| 35 | Regranex | 40 | 75 | | | | 6 |
| 36 | Regranex | 15 | 70 | 90 | 100 | 7.5 | 10 |
| 37 | Regranex | 15 | 70 | 90 | | 18 | |
| 38 | Regranex | 10 | 80 | | | | |
| 39 | Regranex | 40 | 80 | | | | |
| 40 | Regranex | 15 | 50 | 80 | 90 | 15 | 13 |
| 41 | Regranex | 15 | 10 | | | | |
| 42 | Regranex | 5 | 50 | 100 | 100 | 16 | 21 |
| 43 | Regranex | 40 | 70 | 100 | 100 | 22.5 | 10 |
| 44 | Regranex | 5 | 40 | 80 | 100 | 16.5 | 6 |
| 45 | Regranex | | | | | | |
| n | | 14 | 14 | 9 | 8 | 9 | 9 |
| mean | | 19.29 | 59.64 | 87.22 | 95.63 | 14.44 | 10.375 |

TABLE 3-continued

BP, Hydrogel (HG) and Regranex ® Treated Wounds and Percent Wound
Closure (%), Epithelial Thickness (mm) and Degree of Angiogenesis (# Estimated
Capillaries per 20× Field).

|  | Percent (%) Wound Closure | | | | Epi. Thick. (μm) | Angio. (# est. cap/hpf 20×) |
|---|---|---|---|---|---|---|
| Animal # Treatment Group | POD 5 | POD 8 | POD 11 | POD 14 | POD 14 | POD 14 |
| SD | 12.07 | 21.88 | 14.39 | 9.04 | 4.88 | 5.4 |
| SEM | 0.63 | 0.37 | 0.16 | 0.09 | 0.34 | |

The percent closure results can be summarized as follows:

TABLE 4

Summary

|  | POD's | BP (mean) | HG (mean) | REG (mean) |
|---|---|---|---|---|
| wound closure (%) | 0 | 0.00 | 0.00 | 0.00 |
|  | 5 | 13.67 | 13.00 | 19.29 |
|  | 8 | 31.82 | 41.33 | 59.64 |
|  | 11 | 87.00 | 71.92 | 87.22 |
|  | 14 | 96.25 | 89.17 | 95.63 |
| epithelial thickness (mm) | 14 | 11.8 | 13.25 | 14.44 |
| angiogenesis (#/filed) | 14 | 22.9 | 18.45 | 10.38 |

Thus, the BP treatment is as good as REGRENEX™ in closing wounds although slightly slower healing rates are initially observed. BP treatment also shows slightly less thickening of the epithelium and shows considerably improved angiogenesis in the wound area.

Example 4

Future Applications

Because BP has shown promise as a wound healing agent, it will next be tested in applications where wound healing is known to be deficient. Experiments similar to those described above will be performed with diabetic animals to test the healing of full and partial thickness wounds. The response of venous stasis ulcers and diabetic ulcers to BP will also be tested.

In preliminary experiments, Male Sprague Dawley rats weighing greater than 325 g were rendered diabetic by treatment with streptozotocin and the hyperglycemia was confirmed by glucometry. Four full thickness incisional wounds were introduced on the dorsal surface of each animal perpendicular to the longitudinal axis. The wounds were closed with silk sutures and the growth factor or the placebo applied into the wound gap or on top of the incision after closure. The application was done at two time points: 1) on day 0, which is on the day of introducing the wound (surgery) and a second application 2) on day 3 following the introduction of the wound. The incisional strength was measured on day 7 and day 10 after surgery. The data is given in Table 5 and is very encouraging that the BP treatment will be particularly useful in treating a variety of diabetic ulcers, or other wounds characterized by delayed and/or poor healing.

TABLE 5

Tensile Strength of Wounds in Diabetic Rats

| | Tensile Strength (kg/mm) ± sem | |
|---|---|---|
| | Control | BP |
| Day 7 | 3.6 ± 1 | 4.2 ± .7 |
| Day 10 | 5.2 ± .7 | 9.1 ± .8 |

Example 5

Further Characterization of BP

Figure 2:
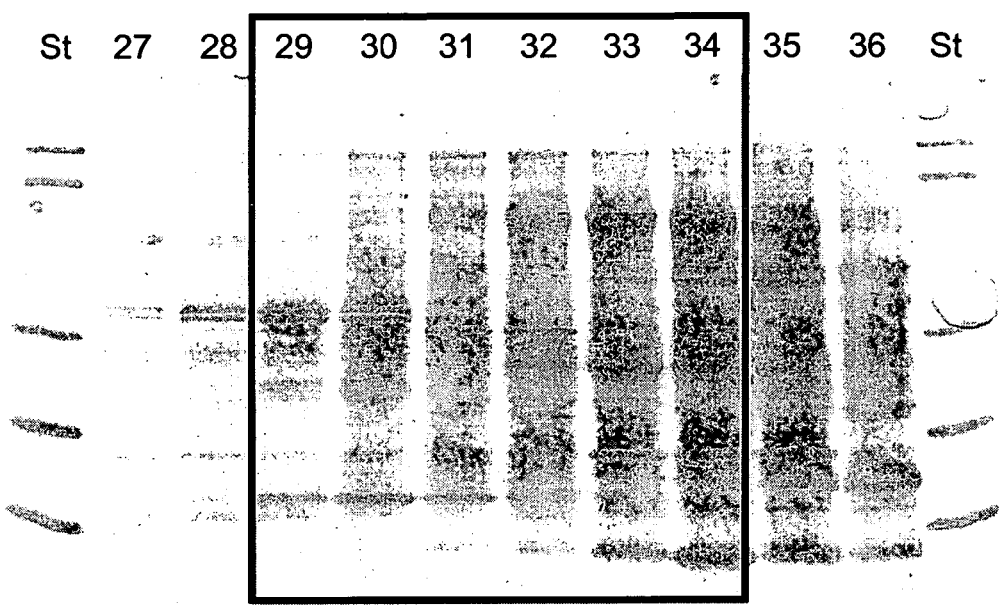
FIG. 2 is an SDS-PAGE gel of HPLC fractions 27–36 of a protein mixture according to an embodiment of the present invention.
Figure 3:
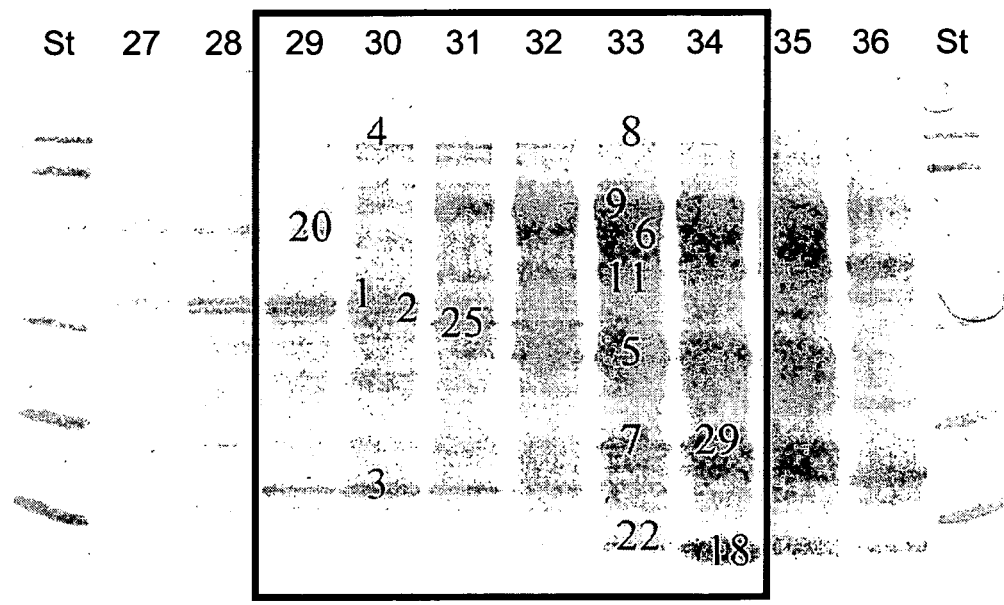
FIG. 3 is an SDS-PAGE gel with identified bands indicated according to the legend of FIG. 4.

The BP has been partially characterized as follows: high performance liquid chromatography ("HPLC") fractions have been denatured, reduced with DTT, and separated by sodium dodecyl sulfate polyacrylamide gel electrophoresis (SDS-PAGE). One minute HPLC fractions from 27 to 36 minutes are shown in FIG. 2. Size standards (ST) of 14, 21, 31, 45, 68 and 97 kDa were obtained as Low Range size standards from BIORAD™ and are shown at either end of the coomassie blue stained gel. In the usual protocol. HPLC fractions 29 through 34 are pooled to produce BP (see boxes, FIGS. 2 and 3), as shown in a similarly prepared SDS-PAGE gel in FIG. 17B.

The various components of the BP were characterized by mass spectrometry and amino acid sequencing of tryptic fragments where there were sufficient levels of protein for analysis. The major bands in the 1D gel (as numerically identified in FIG. 3) were excised, eluted, subjected to tryptic digestion and the fragments were HPLC purified and sequenced. The sequence data was compared against known sequences, and the best matches are shown in FIGS. 15A–B. These identifications are somewhat tentative in that only portions of the entire proteins have been sequenced and, in some cases, there is variation between the human and bovine analogs for a given protein.

Figure 4:
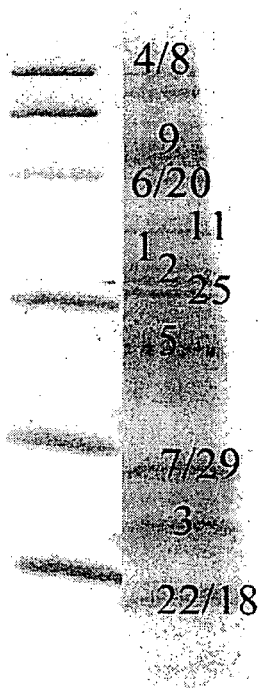
FIG. 4 is an SDS-PAGE gel of a protein mixture according to an embodiment of the present invention with identified bands indicated, as provided in the legend.
Figure 7A:
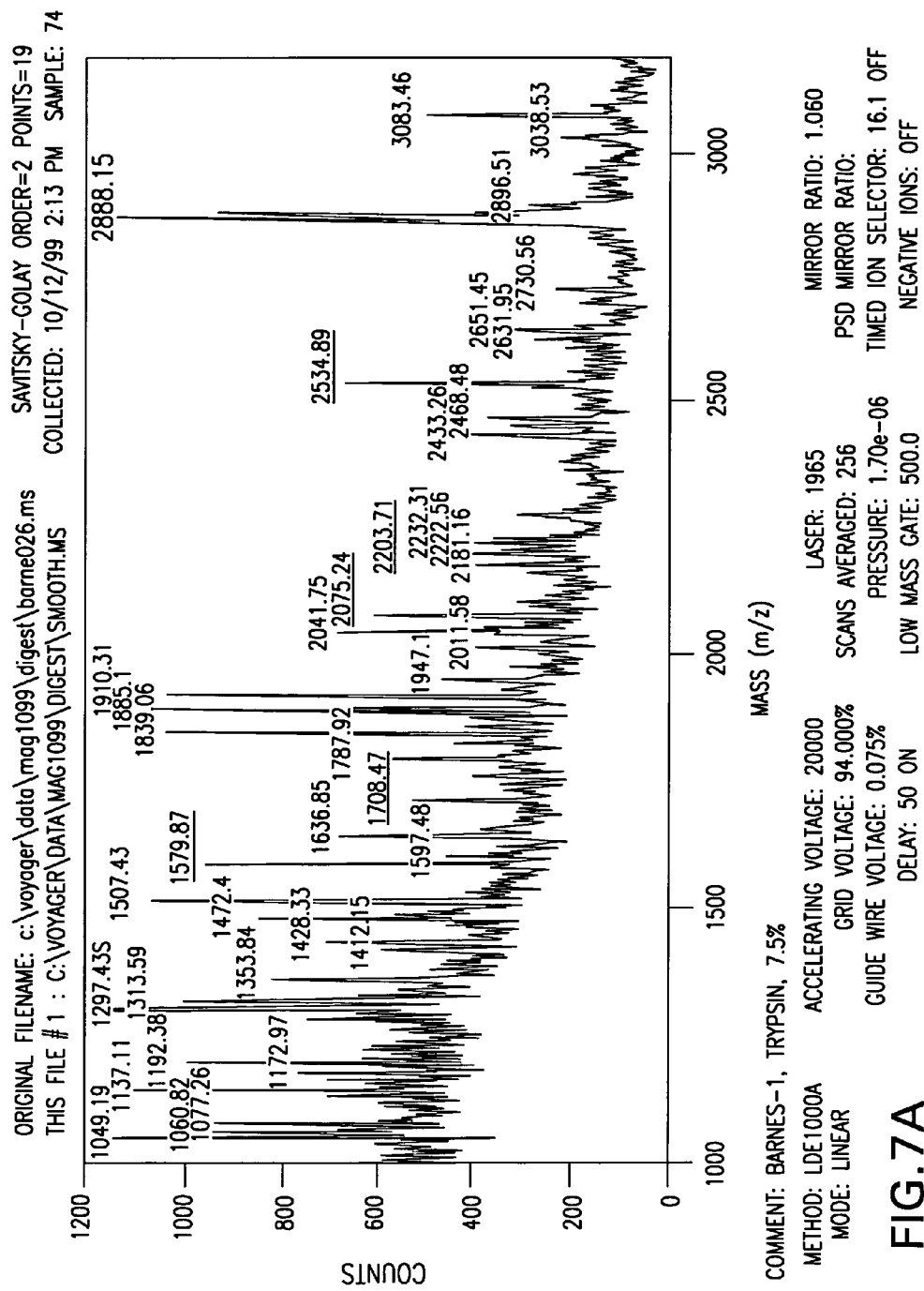
FIGS. 7A–O are mass spectrometer results for tryptic fragments from one dimensional (1-D) gels of a protein mixture according to an embodiment of the present invention.
Figure 7B:
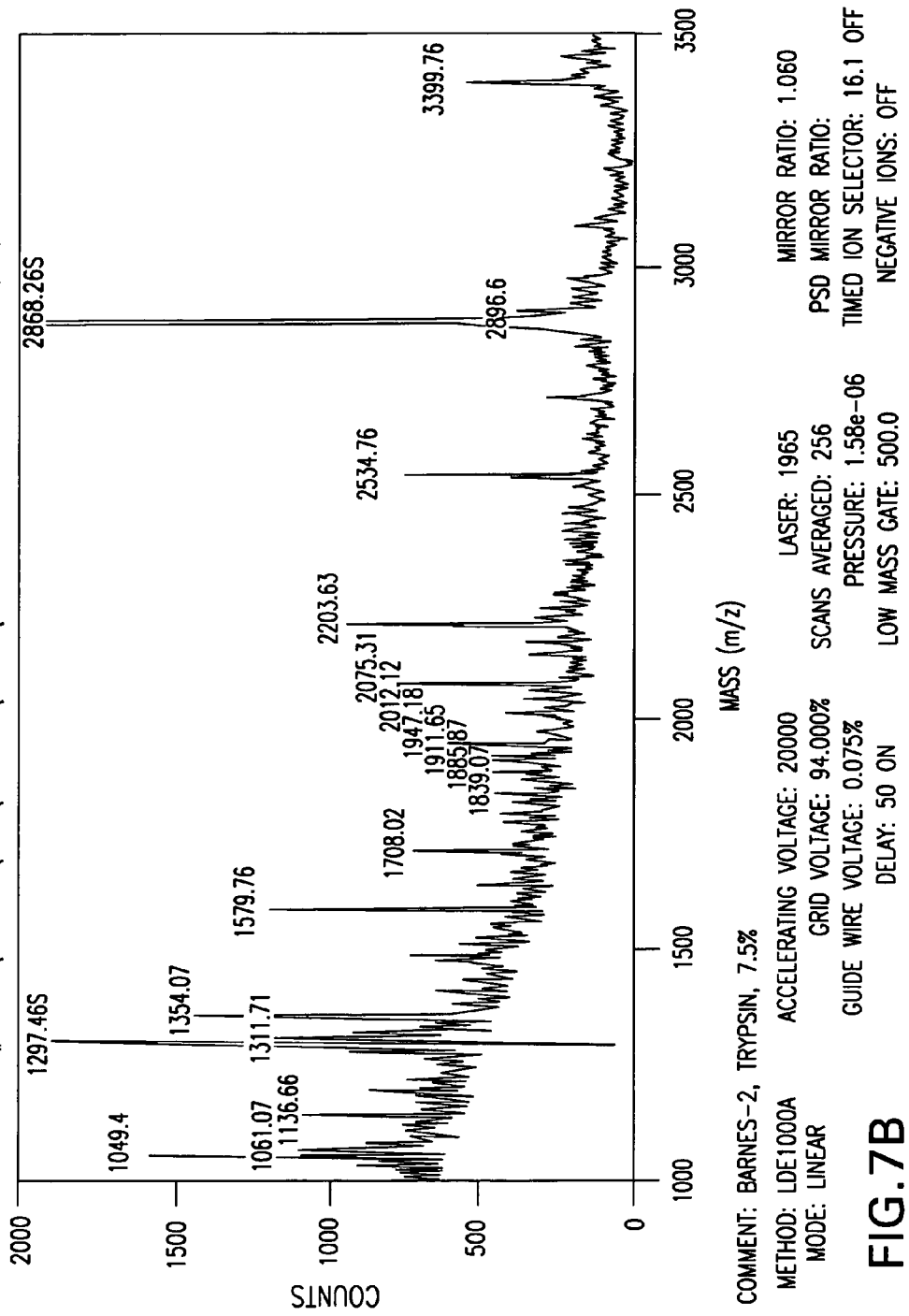
Figure 7C:
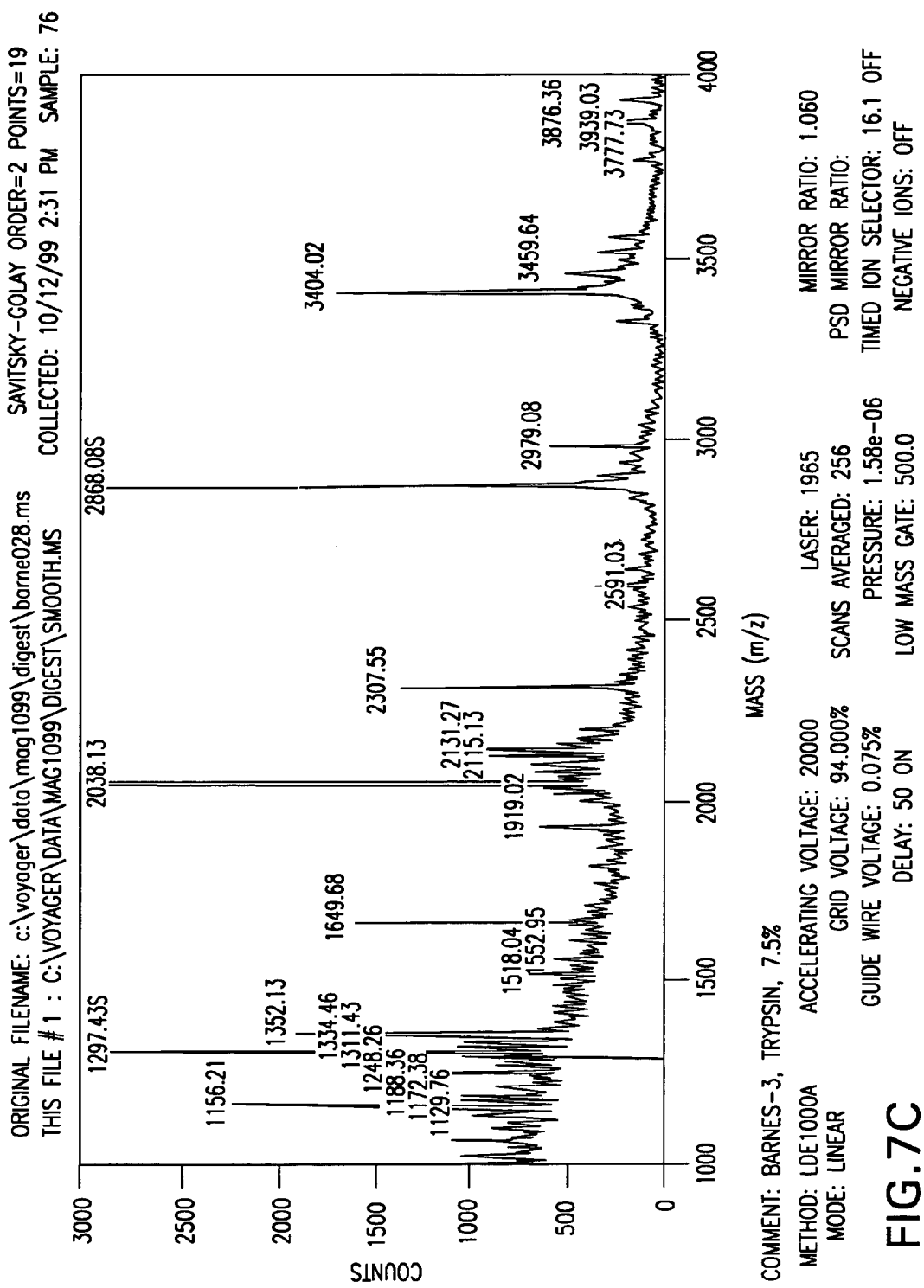
Figure 7D:
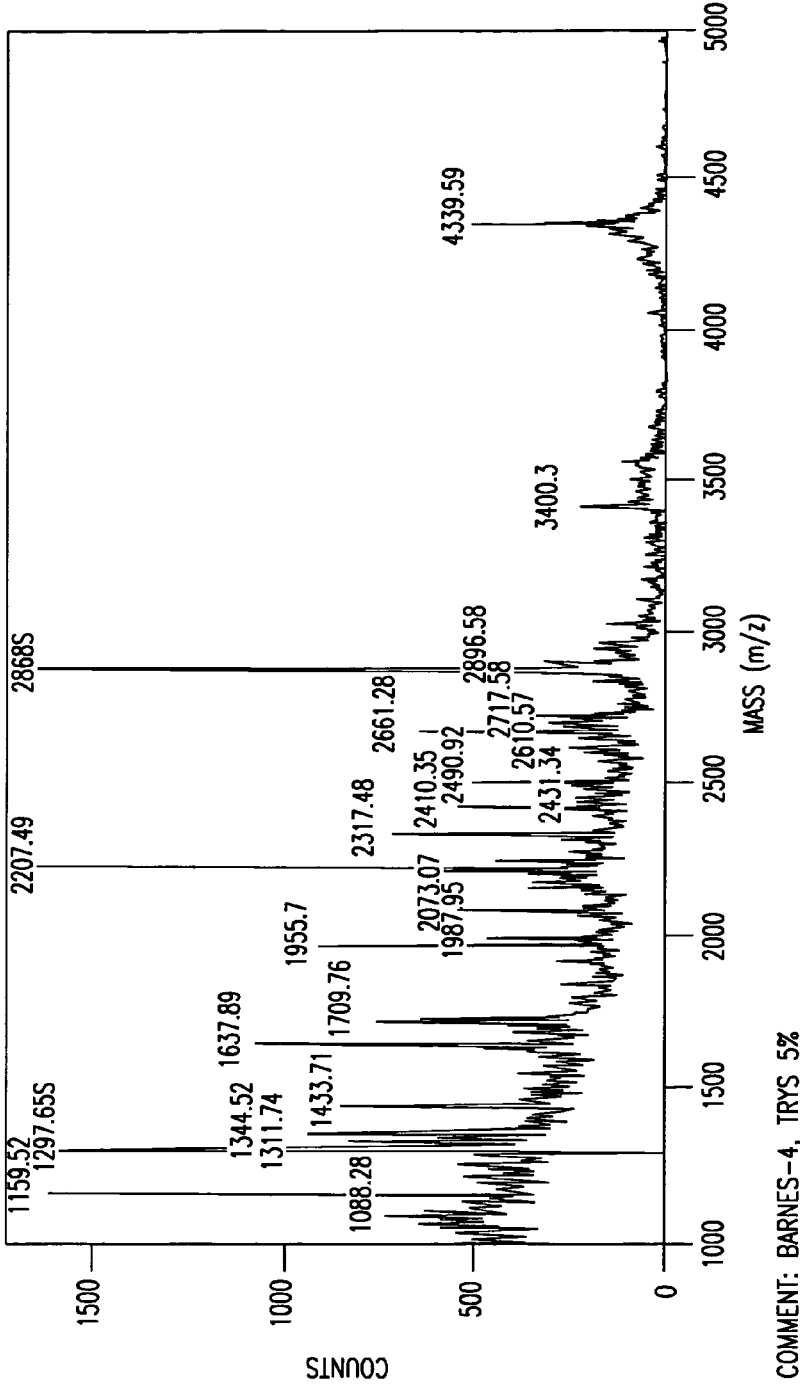
Figure 7E:
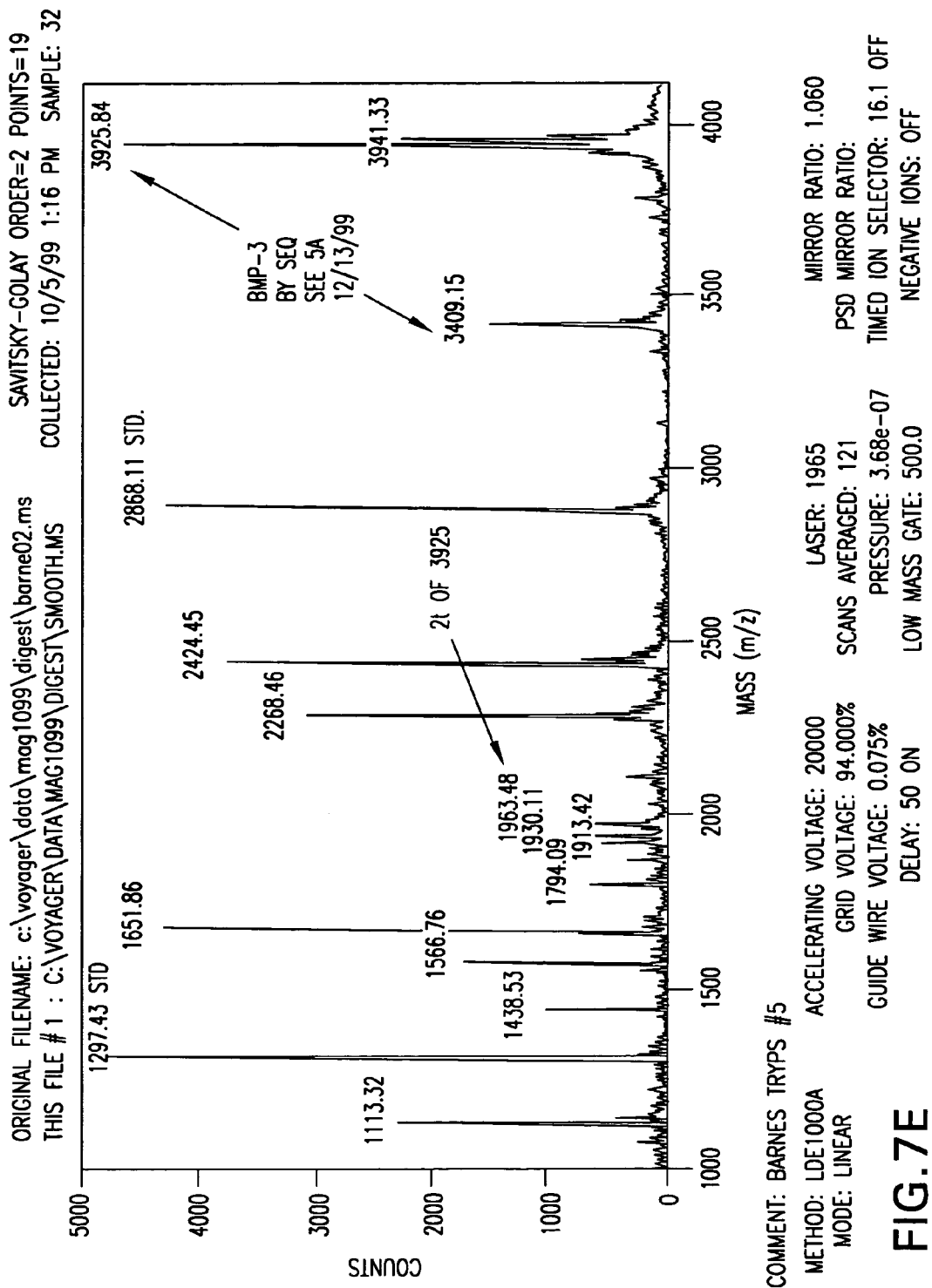
Figure 7F:
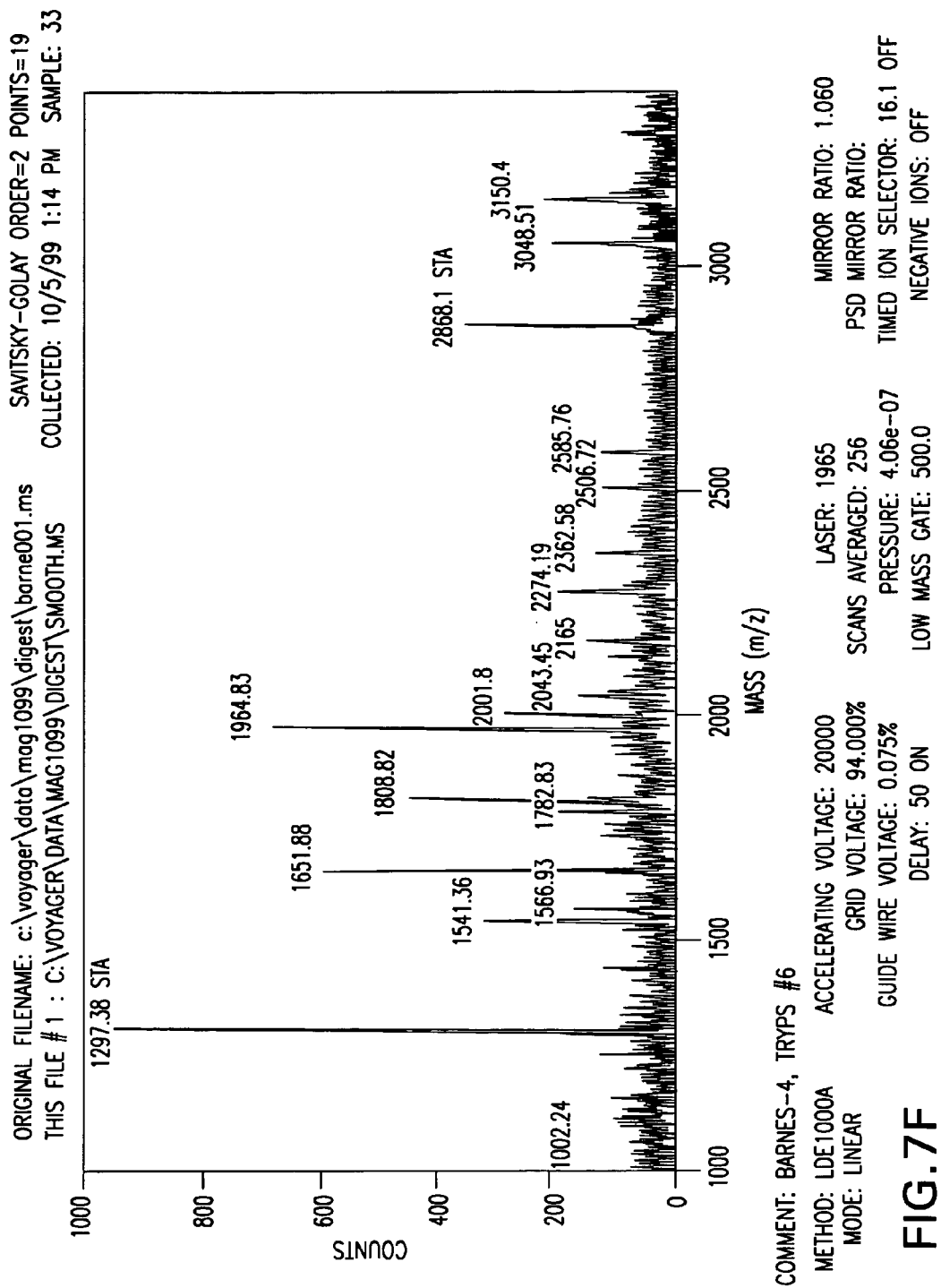
Figure 7G:
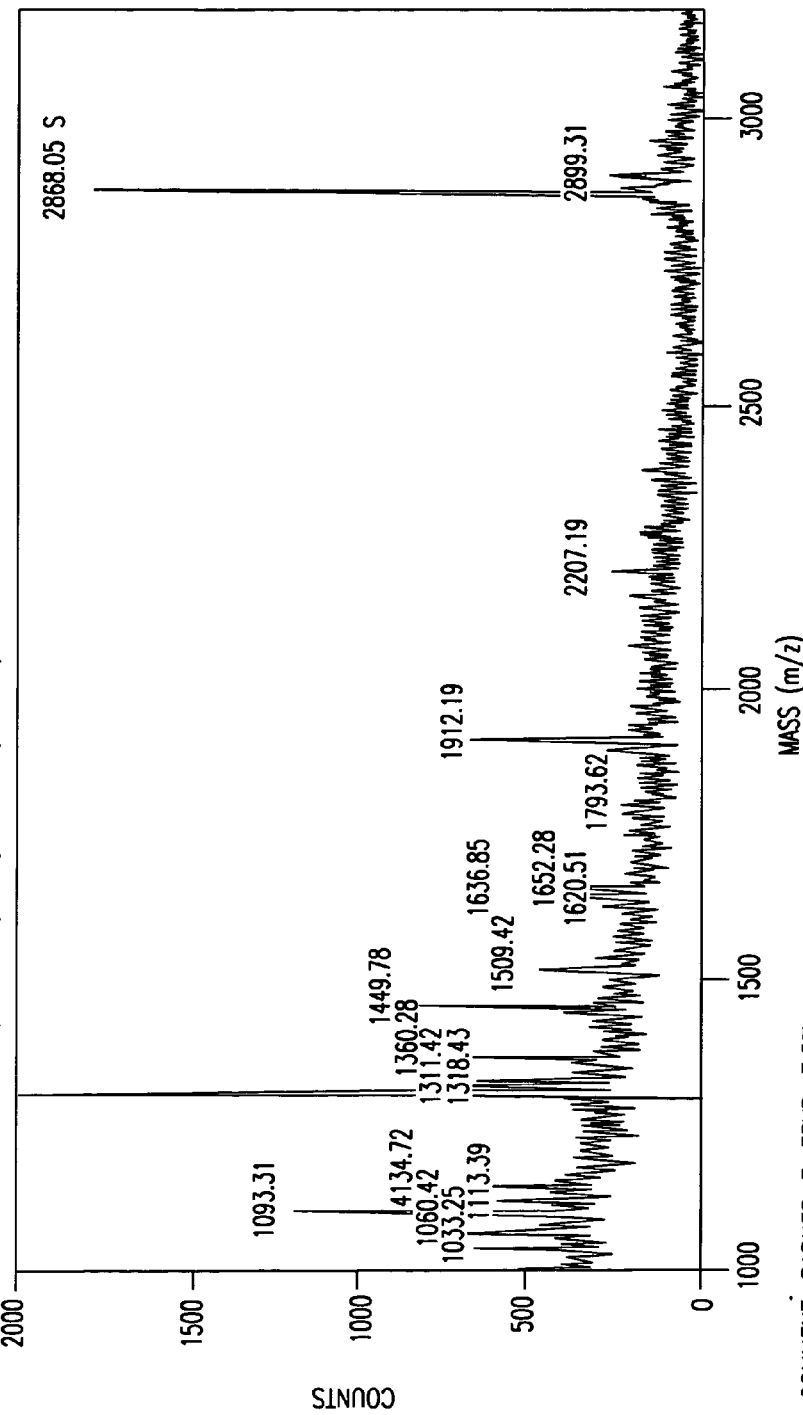
Figure 7H:
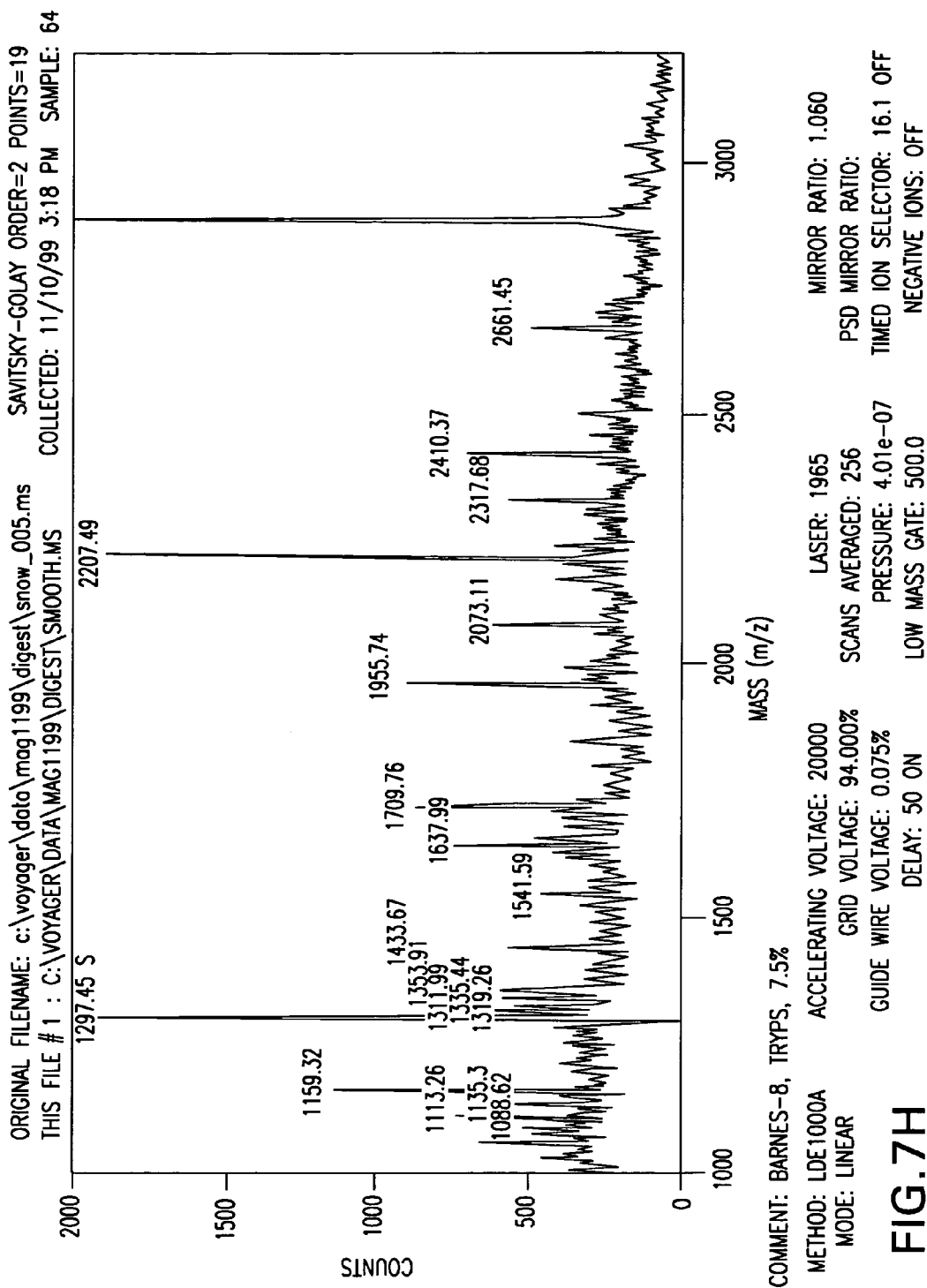
Figure 71:
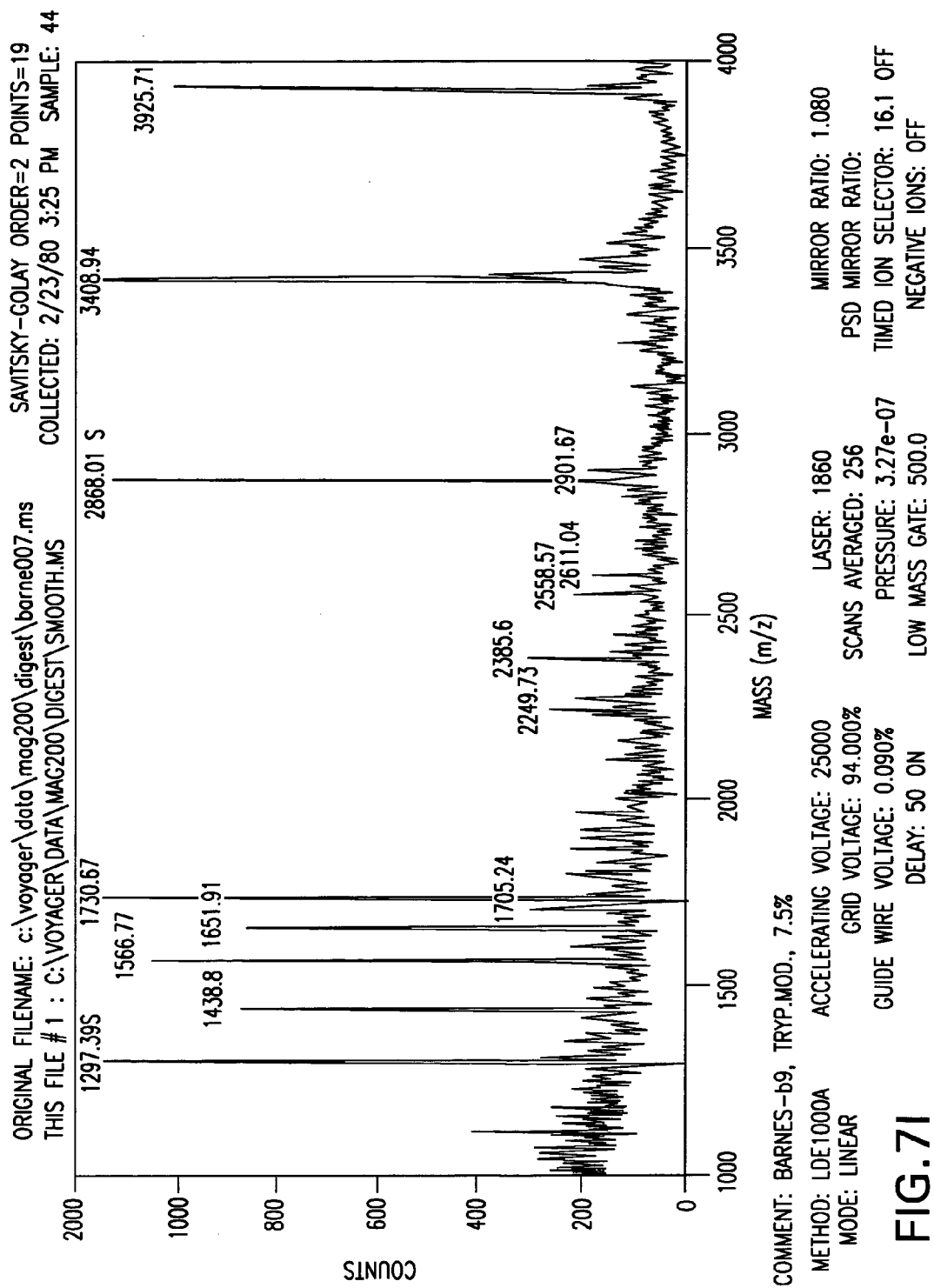
Figure 7J:
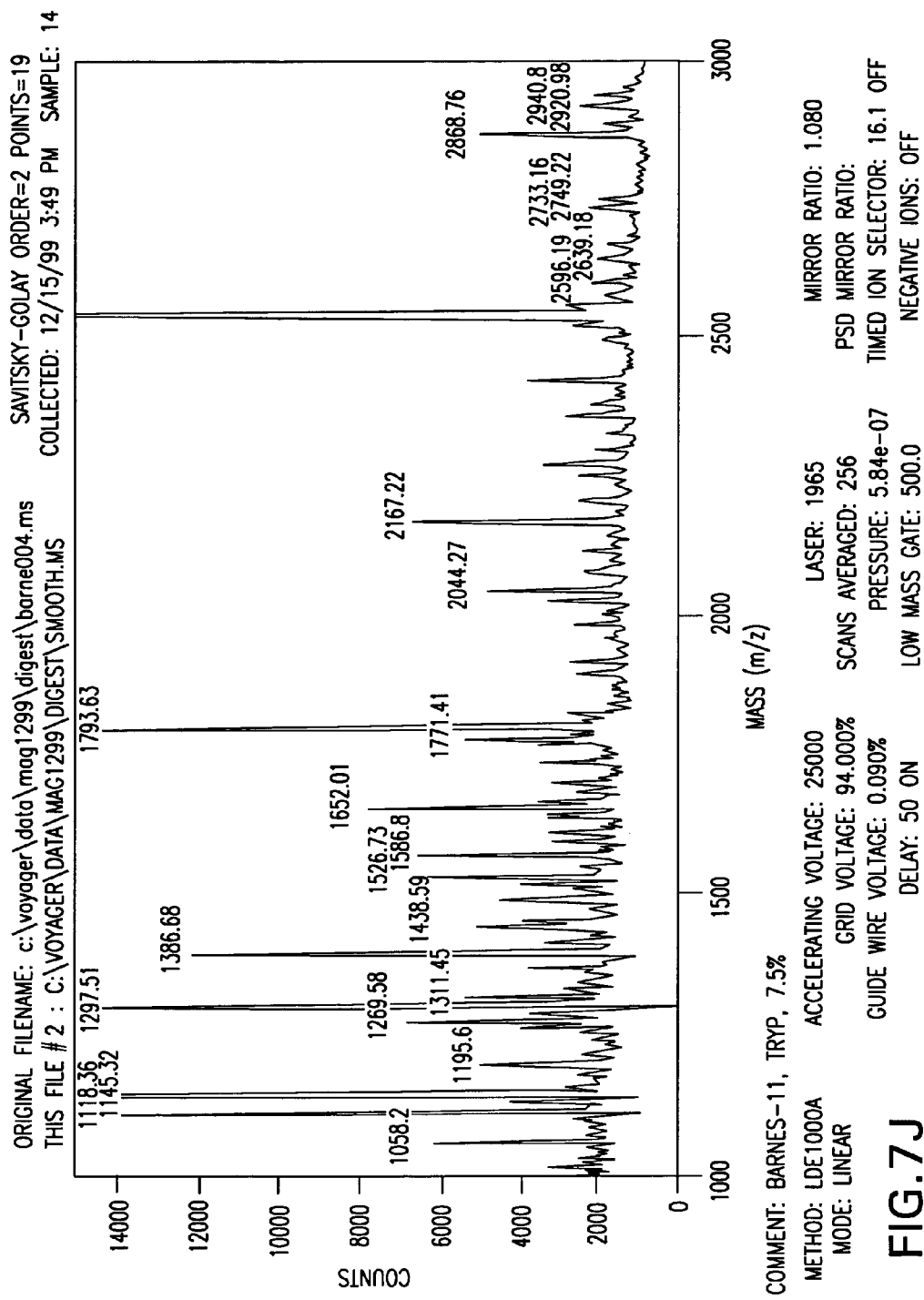
Figure 7K:
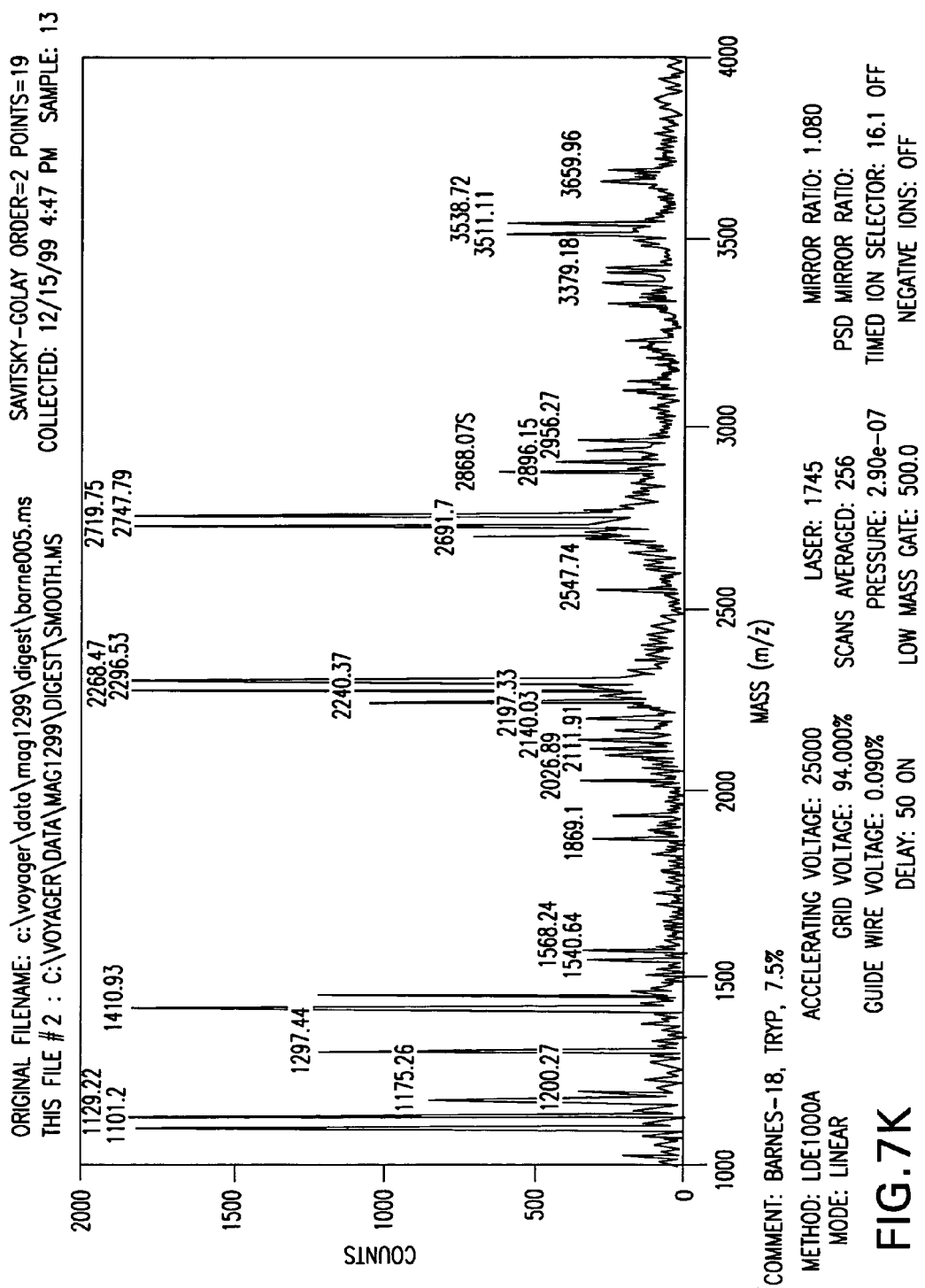
Figure 7L:
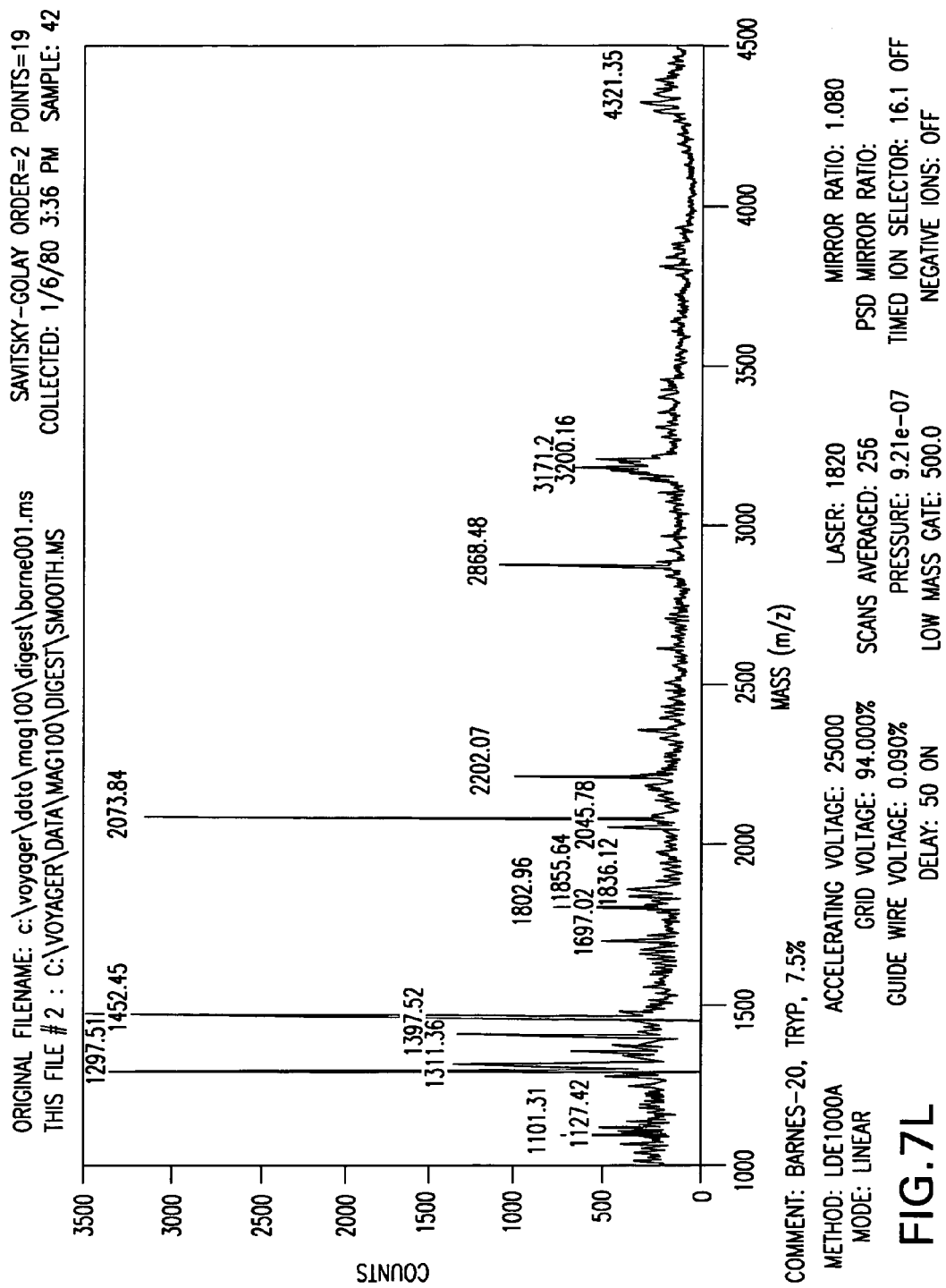
Figure 7M:
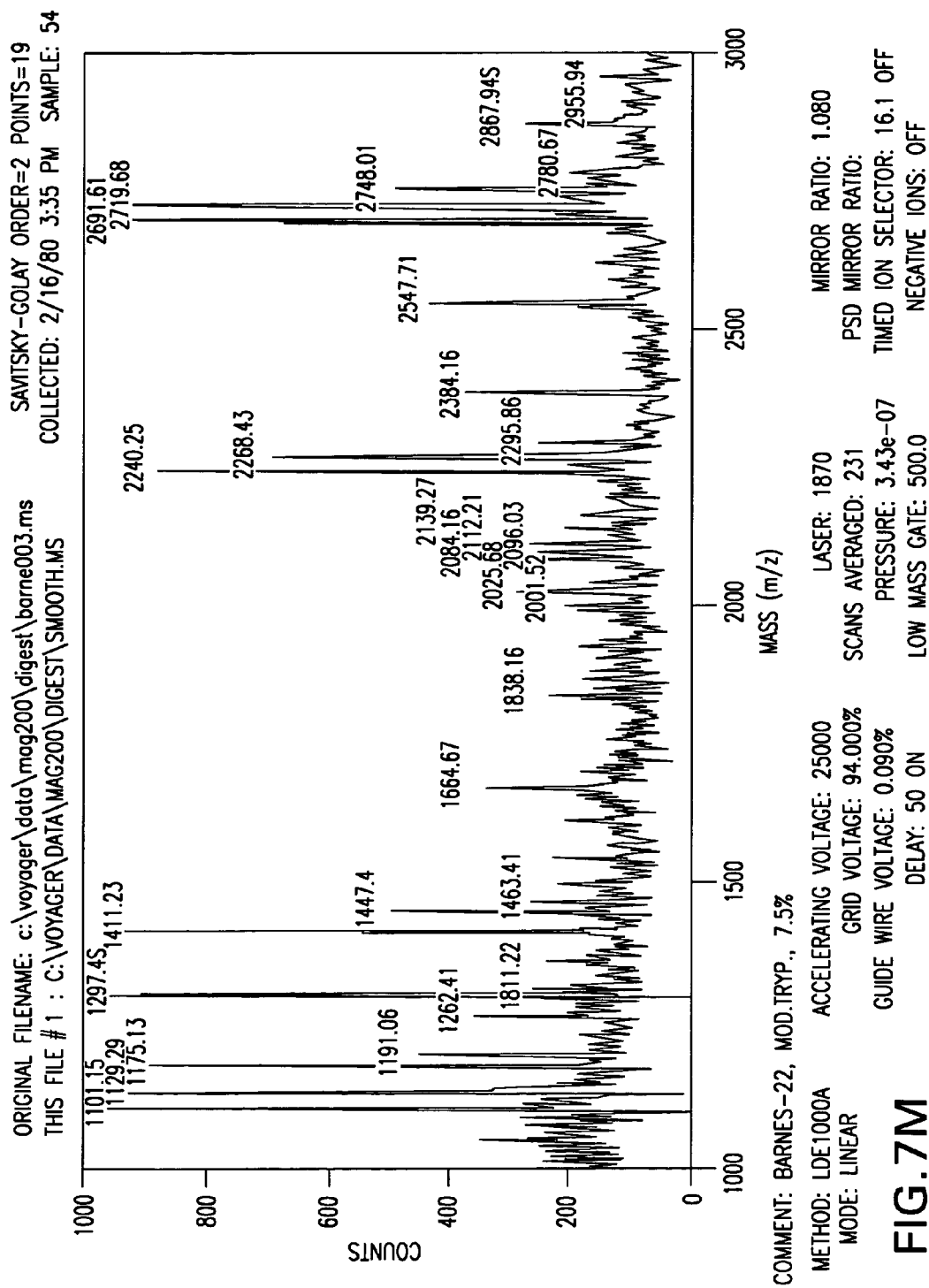
Figure 7N:
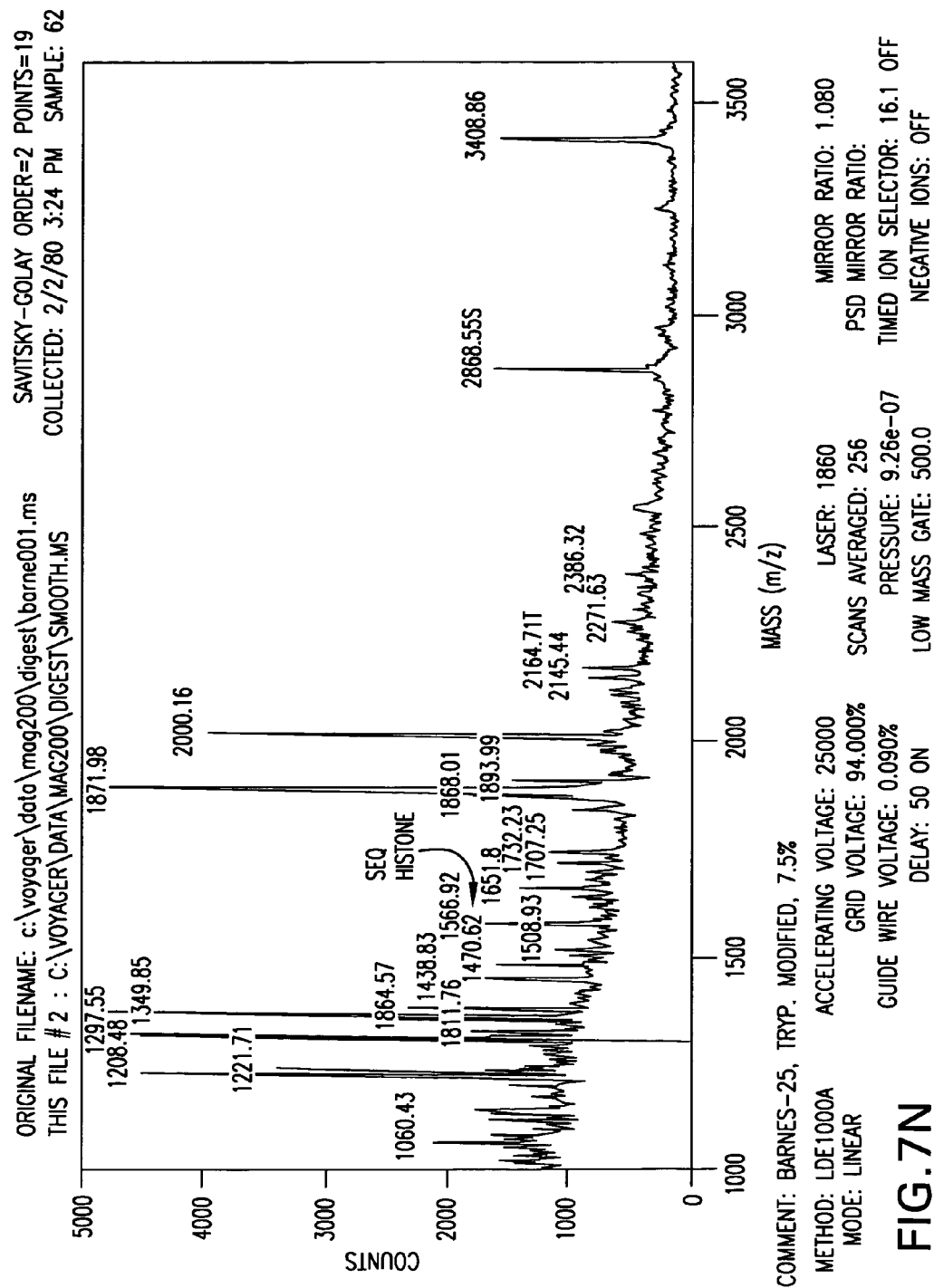
Figure 70:
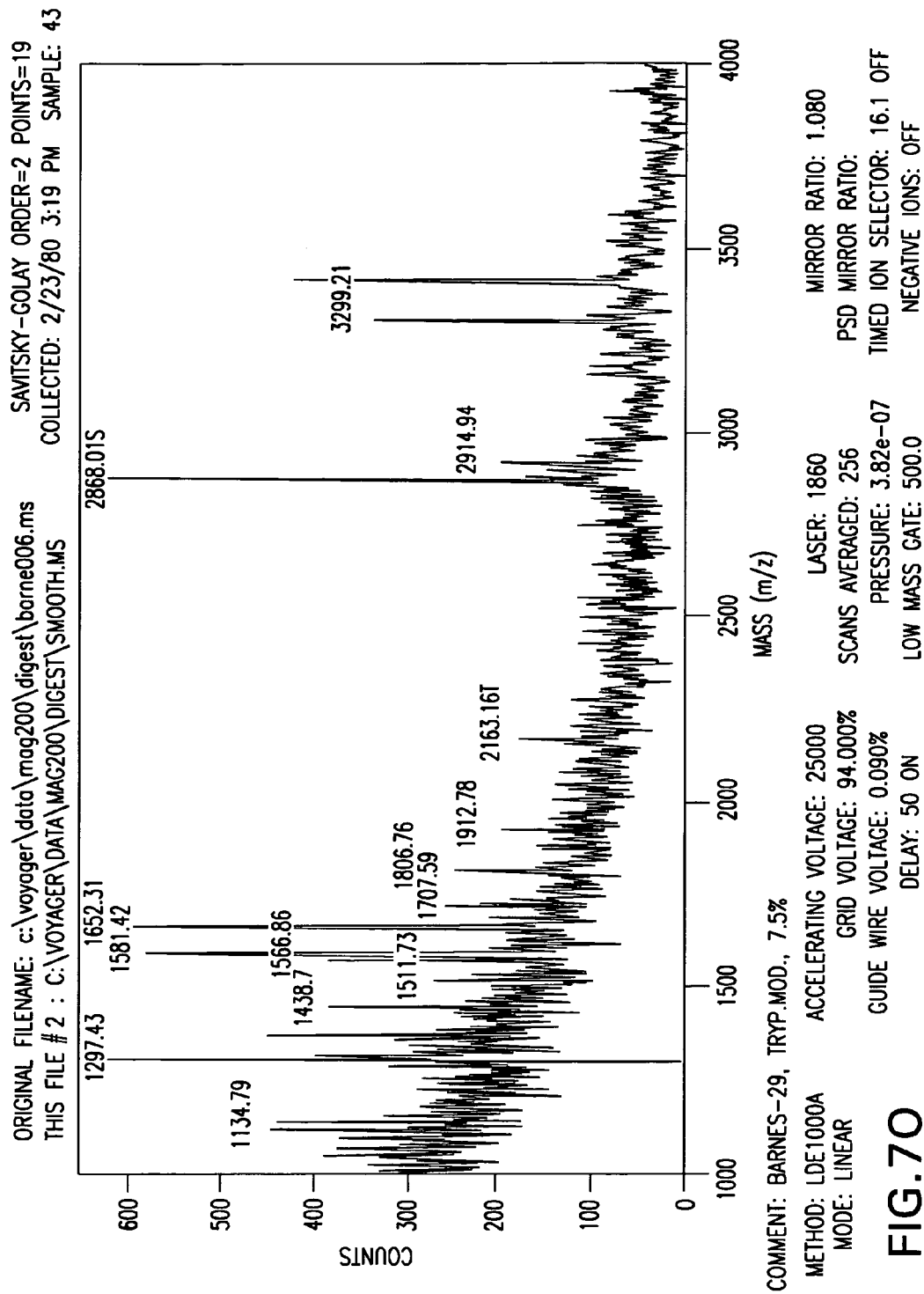

The same tryptic protein fragments were analyzed by mass spectrometry and the mass spectrograms are shown in FIGS. 7A–O. The tabulated results and homologies are shown in FIGS. 16A–F which provides identification information for the bands identified in FIGS. 3–4. As above, assignment of spot identity may be tentative based on species differences and post translational modifications. A summary of all protein identifications from 1D gels is shown in FIG. 4.

The identified protein components of BP, as described in FIGS. 15A–B, 16A–F and 19A–D, were quantified as shown in FIGS. 17A and 17B. FIG. 17B is a stained SDS-PAGE gel of BP and FIG. 17A represents a scanning densitometer trace of the same gel. The identified proteins were labeled and quantified by measuring the area under the curve. These results are presented in FIG. 18 as a percentage of the total peak area.

Thus, there are 11 major bands in the BP SDS-PAGE gel representing about 60% of the protein in BP. The identified proteins fall roughly into three categories: the ribosomal proteins, the histones and growth factors, including bone morphogenic factors (BMPs). It is expected that the ribosomal proteins and histone proteins may be removed from the BP without loss of activity, since these proteins are known to have no growth factor activity. Upon this separation, the specific activity is expected to increase correspondingly.

Experiments are planned to confirm the hypothesis that the histone and ribosomal proteins may be removed from the BP with no resulting loss, or even an increase, in specific activity. Histones will be removed from the BP cocktail by immunoaffinity chromatography using either specific histone protein antibodies or a pan-histone antibody. The histone depleted BP (BP-H) will be tested as described above for wound healing and/or osteogenic activity. Similarly, the known ribosomal proteins will be stripped and the remaining mixture (BP-R) tested.

An SDS-PAGE gel of BP was also analyzed by Western immunoblot with a series of antibodies, as listed in FIG. 14. Visualization of antibody reactivity was by horse radish peroxidase conjugated to a second antibody and using a chemiluminescent substrate. Further, TGF-β1 was quantified using commercially pure TGF-β1 as a standard and was determined to represent less than 1% of the BP protein The antibody analysis indicated that each of the proteins listed in FIG. 14 is present in BP.

Figure 5:
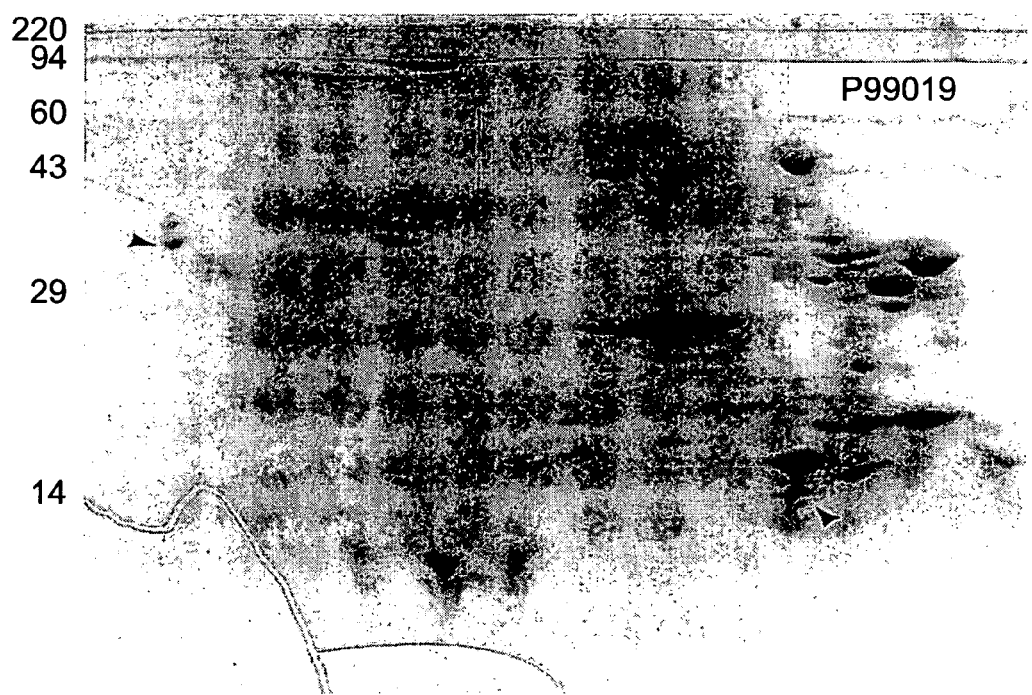
FIG. 5 is two dimensional (2-D) SDS-PAGE gel of a protein mixture according to an embodiment of the present invention with internal standards indicated by arrows.
Figure 6:
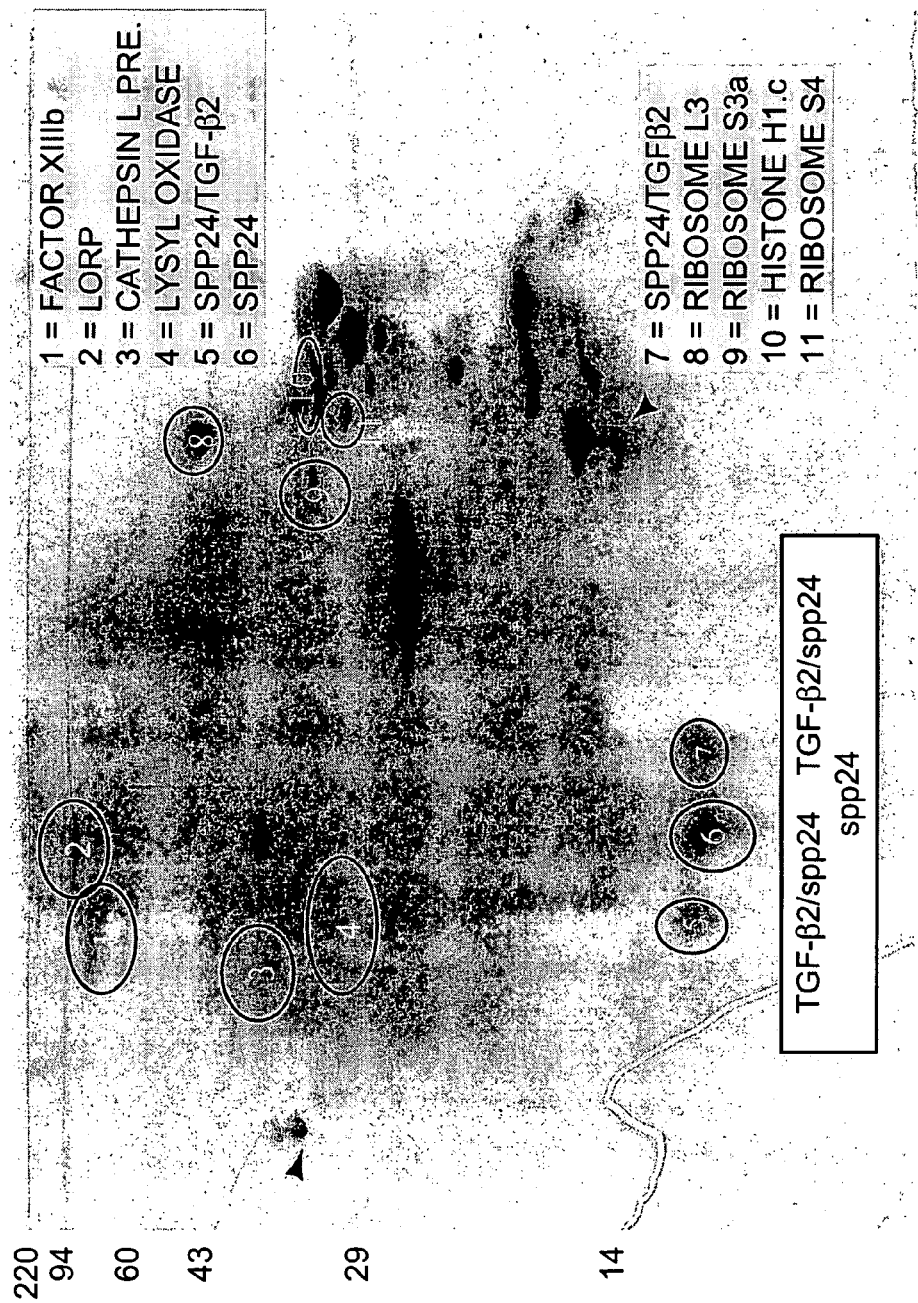
FIG. 6 is a 2-D SDS-PAGE gel of a protein mixture according to an embodiment of the present invention with circled proteins identified as in the legend.

The BP was further characterized by 2-D gel electrophoresis, as shown in FIGS. 5–6. The proteins are separated in horizontal direction according to charge (pI) and in the vertical direction by size as described in two-dimensional electrophoresis adapted for resolution of basic proteins was performed according to the method of O'Farrell et al. (O'Farrell, P. Z., Goodman, H. M. and O'Farrell, P. H., Cell, 12: 1133–1142, 1977) by the Kendrick Laboratory (Madison, Wis.). Two-dimensional gel electrophoresis techniques are known to those of skill in the art. Nonequilibrium pH gradient electrophoresis ("NEPHGE") using 1.5% pH 3.5–10, and 0.25% pH 9–11 ampholines (Amersham Pharmacia Biotech, Piscataway, N.J.) was carried out at 200 V for 12 hrs. Purified tropomyosin (lower spot, 33,000 KDa, pI 5.2), and purified lysozyme (14,000 KDa, pI 10.5–11) (Merck Index) were added to the samples as internal pI markers and are marked with arrows.

After equilibration for 10 min in buffer "0" (10% glycerol, 50 mM dithiothreitol, 2.3% SDS and 0.0625 M tris, pH 6.8) the tube gel was sealed to the top of a stacking gel which is on top of a 12.5% acrylamide slab gel (0.75 mm thick). SDS slab gel electrophoresis was carried out for about 4 hrs at 12.5 mA/gel.

After slab gel electrophoresis two of the gels were coomassie blue stained and the other two were transferred to transfer buffer (12.5 mM Tris, pH 8.8, 86 mM Glycine, 10% MeOH) transblotted onto PVDF paper overnight at 200 mA and approximately 100 volts/two gels. The following proteins (Sigma Chemical Co., St. Louis, Mo.) were added as molecular weight standards to the agarose which sealed the tube gel to the slab gel: myosin (220,000 KDa), phosphorylase A (94,000 KDa), catalase (60,000 KDa), actin (43,000 KDa), carbonic anhydrase (29,000 KDa) and lysozyme (14,000 KDa). FIG. 5 shows the stained 2-D gel with size standards indicated on the left. Tropomyosin (left arrow) and lysozyme (right arrow) are also indicated.

The same gel is shown in FIG. 6 with several identified proteins indicated by numbered circles. The proteins were identified by mass spectrometry and amino acid sequencing of tryptic peptides, as described above. The identity of each of the labeled circles is provided in the legend of FIG. 6 and the data identifying the various protein spots is presented in FIGS. 19A–D.

Figure 8:
FIG. 8 is a 2-D gel Western blot of a protein mixture according to an embodiment of the present invention labeled with anti-phosphotyrosine antibody.

Because several of the proteins migrated at more than one size (e.g., BMP-3 migrating as 6 bands) investigations were undertaken to investigate the extent of post-translation modification of the BP components. Phosphorylation was measured by anti-phosphotyrosine immunoblot and by phosphatase studies. FIG. 8 shows a 2-D gel, electroblotted onto filter paper and probed with a phosphotyrosine mouse monoclonal antibody by SIGMA (# A-5964). Several proteins were thus shown to be phosphorylated at one or more tyrosine residues.

Similar 2-D electroblots were probed with BP component specific antibodies, as shown in FIGS. 9A–D. The filters were probed with BMP-2, BMP-3 (FIG. 9A), BMP-3, BMP-7 (FIG. 9B), BMP-7, BMP-2 (FIG. 9C), and BMP-3 and TGF-β1 (FIG. 9D). Each shows the characteristic, single-size band migrating at varying pI, as is typical of a protein existing in various phosphorylation states.

For the phosphatase studies, BP in 10 mM HCl was incubated overnight at 37° C. with 0.4 units of acid phosphatase (AcP). Treated and untreated samples were added to lyophilized discs of type I collagen and evaluated side by side in the subcutaneous implant rat bioassay, as previously described in U.S. Pat. Nos. 5,290,763, 5,563,124 and 5,371, 191. Briefly, 10 (g of BP in solution was added to lyophilized collagen discs and the discs implanted subcutaneously in the chest of a rat. The discs were then recovered from the rat at 2 weeks for the alkaline phosphotase ("ALP"—a marker for bone and cartilage producing cells) assay or at 3 weeks for histological analysis. For ALP analysis of the samples, the explants were homogenized and levels of ALP activity measured using a commercial kit. For histology, thin sections of the explant were cut with a microtome, and the sections stained and analyzed for bone and cartilage formation.

Figure 10:
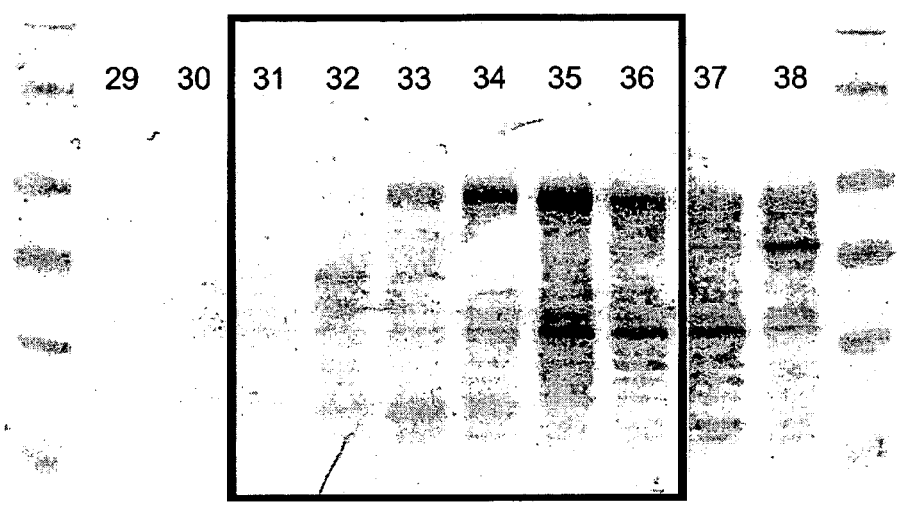
FIG. 10 is a PAS (periodic acid schiff) stained SDS-PAGE gel of HPLC fractions of a protein mixture according to an embodiment of the present invention.
Figure 11:
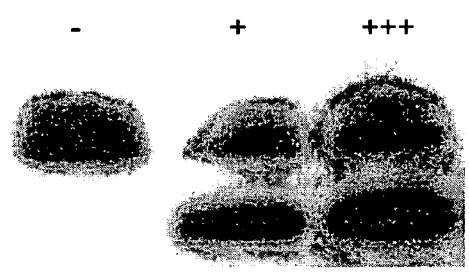
FIG. 11 is an anti-BMP-7 stained SDS-PAGE gel of a PNGase F treated protein mixture according to an embodiment of the present invention.
Figure 12:
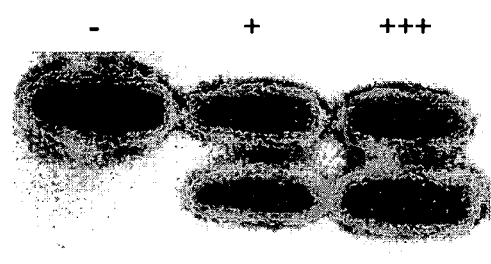
FIG. 12 is an anti-BMP-2 stained SDS-PAGE gel of a PNGase F treated protein mixture according to an embodiment of the present invention.
Figure 13A:
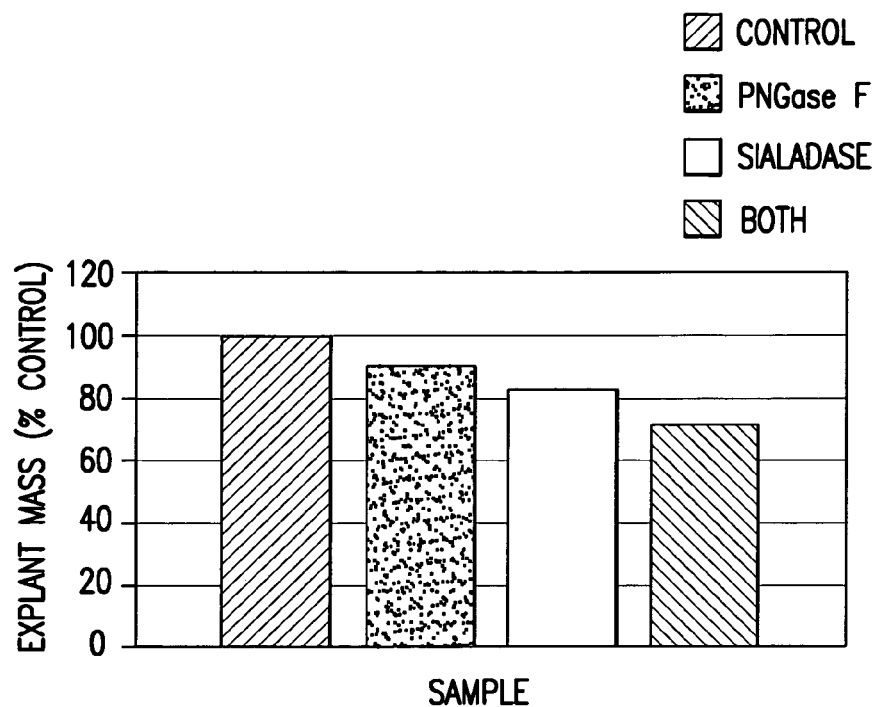
FIGS. 13A–B are bar charts showing explant mass of glycosylated components in a protein mixture according to an embodiment of the present invention (FIG. 13A) and ALP score (FIG. 13B) of the same components.
Figure 13B:
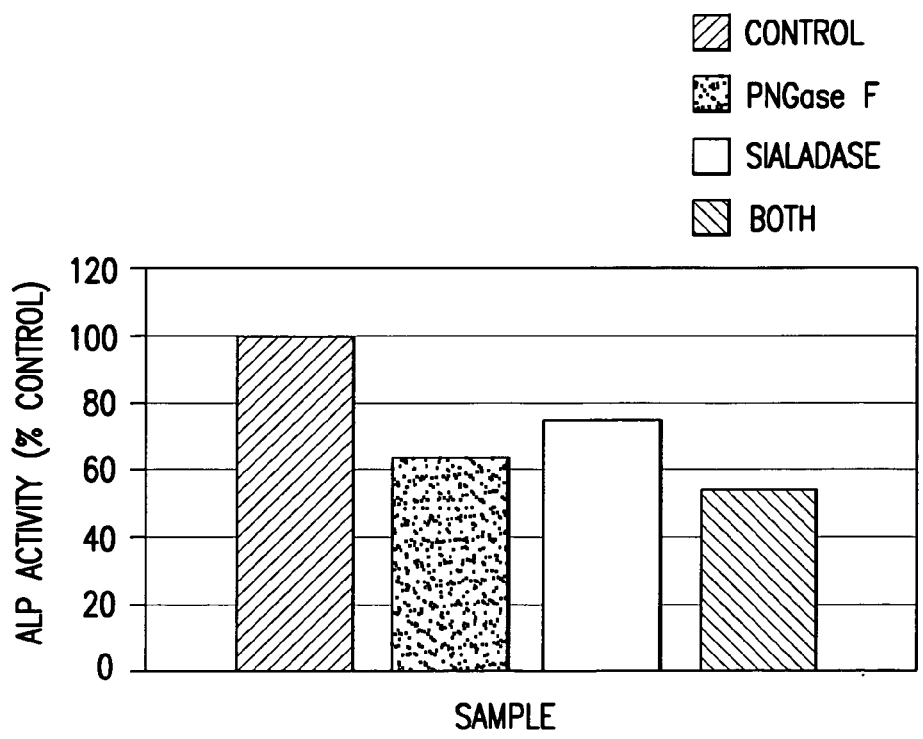

Both native- and phosphatase-treated BP samples were assayed for morphogenic activity by mass of the subcutaneous implant (explant mass) and ALP score. The results showed that AcP treatment reduced the explant mass and ALP score from 100% to about 60%. Thus, phosphorylation is important for BP activity. The BP was also analyzed for glycosylation. FIG. 10 shows an SDS-PAGE gel stained with periodic acid schiff (PAS)—a non-specific carbohydrate stain, indicating that several of the BP components are glycosylated (starred protein identified as BMP-3). FIGS. 11–12 show immunodetection of two specific proteins (BMP-7, FIG. 11 and BMP-2, FIG. 12) treated with increasing levels of PNGase F (Peptide-N-Glycosidase F). Both BMP-2 and BMP-7 show some degree of glycoslyation in BP, but appear to have some level of protein resistant to PNGase F as well (plus signs indicate increasing levels of enzyme). Functional activity of PNGase F and sialadase treated samples were assayed by explant mass and by ALP score, as shown in FIGS. 13A and 13B which shows that glycosylation is required for full activity.

In summary, BMPs 2, 3 and 7 are modified by phosphorylation and glycosylation. These post-translation modifications affect protein morphogenic activity, 33% and 50% repectively, and care must be taken in preparing BP not to degrade these functional derivatives.

What is claimed is:

1. A method of promoting the healing of a skin wound comprising applying to said skin wound an effective skin wound healing amount of a composition comprising:
   BP (bone protein mixture) from which histones and/or ribosomes have been excluded and comprising
   the growth factors BMP-3 and TGF-β2, and
   a pharmaceutically acceptable carrier.

2. The method of claim 1 wherein the composition further comprises at least one bone-derived growth factor selected from the group consisting of BMP-2, BMP-4, BMP-5, BMP-6, and BMP-7, wherein at least one said growth factor retains native post-translation modifications.

3. The method of claim 1 wherein the composition further comprises at least one bone-derived growth factor selected from the group consisting of FGF-1, TGF-β1, and TGF-β3 in its native post-translation modified form.

4. The method of claim 1 wherein at least one said growth factor is at least partially phosphorylated and glycosylated.

5. The method of claim 1, wherein histone proteins H1c and H1x are excluded from the composition.

6. A method of promoting skin wound healing comprising applying to said skin wound a composition comprising a mixture of growth factors comprising BMP-2, BMP-3, BMP-6, and TGF-β2 in a pharmaceutically acceptable carrier.

7. The method of claim 1 wherein ribosomal proteins LORP, Lg, s20, L3, S3a, S4 and L32 are excluded from the composition.

8. The method of claim 1 wherein said at least one growth factor is derived from bovine bone and is at least partially phosphorylated and glycosylated.

9. A method of improving angiogenesis in a wound area where osteogenesis is not desired comprising applying to said wound a composition comprising a bone protein mixture, wherein when said mixture is subjected to sodium dodecyl sulfate polyacrylamide gel electrophoresis, yields a reduced or non-reduced protein band pattern as identified in FIG. 1, said composition including a pharmaceutically acceptable carrier.

10. The method of claim 1 wherein said bone protein mixture is obtained from bovine bone, and, when subjected to trypsin digestion, comprises the following tryptic peptide fragments:
STGVLLPLQNNELPG (SEQ ID NO:4)
STGVLLPLQNNELPGAEYQY (SEQ ID NO:5)
STGVLLPLQ (SEQ ID NO:6)
QTLQFXE (SEQ ID NO:7)
VYAF (SEQ ID NO:8)
HAGKYSREKNTA (SEQ ID NO:9)
SQTLQFDEQ (SEQ ID NO:10)
SLKPSNHA (SEQ ID NO:11)
XALFAQLGXALGPI (SEQ ID NO:13)
SQTLQFDEQT (SEQ ID NO:14)
SQTLXF (SEQ ID NO:15)
ALDAAYCFR (SEQ ID NO:19)
GYNANFCAGACPYL (SEQ ID NO:20)
VNSQSLSPY (SEQ ID NO:21)
SQTLQFXE (SEQ ID NO:23)
XALFGAQLGXALGPI (SEQ ID NO:24)
HAGKYSREKNTAP (SEQ ID NO:26)
HAGKYSREKNTPA (SEQ ID NO:27)
HAGKYSREKNTPAP (SEQ ID NO:28).

11. The method of claim 1 wherein said skin wound comprises a diabetic ulcer.

12. The method of claim 1, wherein the BP is prepared by a process comprising protein extraction from demineralized bone, filtration, and chromatography.

13. The method of claim 12, wherein the filtration comprises first ultrafiltration with an ultrafiltration membrane having a nominal molecular weight cut off (MWCO) of 100 kD, to yield a retentate and a filtrate, and second ultrafiltration of the filtrate with an ultrafiltration membrane having a nominal MWCO of about 10 kD.

14. The method of claim 12, wherein the chromatography comprises anion exchange chromatography, cation exchange chromatography, and HPLC in which the BP is eluted from the column with an organic solvent/water mixture gradient.

15. The method of claim 1, wherein the bone protein mixture is extracted from demineralized bone.

16. The method of claim 1, wherein at least one protein other than BMP-3 and TGF-β2 has been excluded from the bone protein mixture.

17. The method of claim 1, wherein when the bone protein mixture is subjected to sodium dodecyl sulfate polyacrylamide gel electrophoresis it yields a reduced or non-reduced protein band pattern as identified in any one of FIGS. 1–4.

18. The method of claim 15, wherein the bone protein mixture is subjected to chromatography.

19. The method of claim 18, wherein the bone protein mixture comprises at least one fraction eluted during chromatography.

* * * * *

SEQUENCE LISTING

<160> NUMBER OF SEQ ID NOS: 33

<210> SEQ ID NO 1
<211> LENGTH: 11
<212> TYPE: PRT
<213> ORGANISM: Bos indicus
<220> FEATURE:
<221> NAME/KEY: misc_feature
<222> LOCATION: (1)..(1)
<223> OTHER INFORMATION: Xaa can be any naturally occurring amino acid

<400> SEQUENCE: 1

Xaa Leu Ala Ala Ala Gly Tyr Asp Val Glu Lys
1               5                   10

<210> SEQ ID NO 2
<211> LENGTH: 11
<212> TYPE: PRT
<213> ORGANISM: Bos indicus

<400> SEQUENCE: 2

Ser Leu Glu Lys Val Cys Ala Asp Leu Ile Arg
1               5                   10

<210> SEQ ID NO 3
<211> LENGTH: 13
<212> TYPE: PRT
<213> ORGANISM: Bos indicus

<400> SEQUENCE: 3

Val Cys Gly Met Leu Gly Phe Pro Ser Glu Ala Pro Val
1               5                   10

<210> SEQ ID NO 4
<211> LENGTH: 15
<212> TYPE: PRT
<213> ORGANISM: Bos indicus

<400> SEQUENCE: 4

Ser Thr Gly Val Leu Leu Pro Leu Gln Asn Asn Glu Leu Pro Gly
1               5                   10                  15

<210> SEQ ID NO 5
<211> LENGTH: 20
<212> TYPE: PRT
<213> ORGANISM: Bos indicus

<400> SEQUENCE: 5

Ser Thr Gly Val Leu Leu Pro Leu Gln Asn Asn Glu Leu Pro Gly Ala
1               5                   10                  15

Glu Tyr Gln Tyr
            20

<210> SEQ ID NO 6
<211> LENGTH: 9
<212> TYPE: PRT
<213> ORGANISM: Bos indicus

<400> SEQUENCE: 6

Ser Thr Gly Val Leu Leu Pro Leu Gln
1               5

```
<210> SEQ ID NO 7
<211> LENGTH: 7
<212> TYPE: PRT
<213> ORGANISM: Bos indicus
<220> FEATURE:
<221> NAME/KEY: misc_feature
<222> LOCATION: (6)..(6)
<223> OTHER INFORMATION: Xaa can be any naturally occurring amino acid

<400> SEQUENCE: 7

Gln Thr Leu Gln Phe Xaa Glu
1               5

<210> SEQ ID NO 8
<211> LENGTH: 4
<212> TYPE: PRT
<213> ORGANISM: Bos indicus

<400> SEQUENCE: 8

Val Tyr Ala Phe
1

<210> SEQ ID NO 9
<211> LENGTH: 12
<212> TYPE: PRT
<213> ORGANISM: Bos indicus

<400> SEQUENCE: 9

His Ala Gly Lys Tyr Ser Arg Glu Lys Asn Thr Ala
1               5                   10

<210> SEQ ID NO 10
<211> LENGTH: 9
<212> TYPE: PRT
<213> ORGANISM: Bos indicus

<400> SEQUENCE: 10

Ser Gln Thr Leu Gln Phe Asp Glu Gln
1               5

<210> SEQ ID NO 11
<211> LENGTH: 8
<212> TYPE: PRT
<213> ORGANISM: Bos indicus

<400> SEQUENCE: 11

Ser Leu Lys Pro Ser Asn His Ala
1               5

<210> SEQ ID NO 12
<211> LENGTH: 7
<212> TYPE: PRT
<213> ORGANISM: Bos indicus

<400> SEQUENCE: 12

Ala Ile Val Glu Arg Tyr Val
1               5

<210> SEQ ID NO 13
<211> LENGTH: 14
<212> TYPE: PRT
<213> ORGANISM: Bos indicus
<220> FEATURE:
<221> NAME/KEY: misc_feature
<222> LOCATION: (1)..(1)
<223> OTHER INFORMATION: Xaa can be any naturally occurring amino acid
```

-continued

```
<220> FEATURE:
<221> NAME/KEY: misc_feature
<222> LOCATION: (9)..(9)
<223> OTHER INFORMATION: Xaa can be any naturally occurring amino acid

<400> SEQUENCE: 13

Xaa Ala Leu Phe Ala Gln Leu Gly Xaa Ala Leu Gly Pro Ile
1               5                   10

<210> SEQ ID NO 14
<211> LENGTH: 10
<212> TYPE: PRT
<213> ORGANISM: Bos indicus

<400> SEQUENCE: 14

Ser Gln Thr Leu Gln Phe Asp Glu Gln Thr
1               5                   10

<210> SEQ ID NO 15
<211> LENGTH: 6
<212> TYPE: PRT
<213> ORGANISM: Bos indicus
<220> FEATURE:
<221> NAME/KEY: misc_feature
<222> LOCATION: (5)..(5)
<223> OTHER INFORMATION: Xaa can be any naturally occurring amino acid

<400> SEQUENCE: 15

Ser Gln Thr Leu Xaa Phe
1               5

<210> SEQ ID NO 16
<211> LENGTH: 13
<212> TYPE: PRT
<213> ORGANISM: Bos indicus

<400> SEQUENCE: 16

Val Leu Ala Thr Val Thr Lys Pro Val Gly Gly Asp Lys
1               5                   10

<210> SEQ ID NO 17
<211> LENGTH: 5
<212> TYPE: PRT
<213> ORGANISM: Bos indicus
<220> FEATURE:
<221> NAME/KEY: misc_feature
<222> LOCATION: (1)..(1)
<223> OTHER INFORMATION: Xaa can be any naturally occurring amino acid

<400> SEQUENCE: 17

Xaa Val Phe Ala Leu
1               5

<210> SEQ ID NO 18
<211> LENGTH: 10
<212> TYPE: PRT
<213> ORGANISM: Bos indicus

<400> SEQUENCE: 18

Ala Val Pro Gln Leu Gln Gly Tyr Leu Arg
1               5                   10

<210> SEQ ID NO 19
<211> LENGTH: 9
<212> TYPE: PRT
<213> ORGANISM: Bos indicus
```

```
<400> SEQUENCE: 19

Ala Leu Asp Ala Ala Tyr Cys Phe Arg
1               5

<210> SEQ ID NO 20
<211> LENGTH: 14
<212> TYPE: PRT
<213> ORGANISM: Bos indicus

<400> SEQUENCE: 20

Gly Tyr Asn Ala Asn Phe Cys Ala Gly Ala Cys Pro Tyr Leu
1               5                   10

<210> SEQ ID NO 21
<211> LENGTH: 9
<212> TYPE: PRT
<213> ORGANISM: Bos indicus

<400> SEQUENCE: 21

Val Asn Ser Gln Ser Leu Ser Pro Tyr
1               5

<210> SEQ ID NO 22
<211> LENGTH: 7
<212> TYPE: PRT
<213> ORGANISM: Bos indicus

<400> SEQUENCE: 22

Lys Ala Ala Lys Pro Ser Val
1               5

<210> SEQ ID NO 23
<211> LENGTH: 8
<212> TYPE: PRT
<213> ORGANISM: Bos indicus
<220> FEATURE:
<221> NAME/KEY: misc_feature
<222> LOCATION: (7)..(7)
<223> OTHER INFORMATION: Xaa can be any naturally occurring amino acid

<400> SEQUENCE: 23

Ser Gln Thr Leu Gln Phe Xaa Glu
1               5

<210> SEQ ID NO 24
<211> LENGTH: 15
<212> TYPE: PRT
<213> ORGANISM: Bos indicus
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 24

Xaa Ala Leu Phe Gly Ala Gln Leu Gly Xaa Ala Leu Gly Pro Ile
1               5                   10                  15

<210> SEQ ID NO 25
<211> LENGTH: 14
<212> TYPE: PRT
<213> ORGANISM: Bos indicus
```

```
<400> SEQUENCE: 25

Val Val Cys Gly Met Leu Gly Phe Pro Ser Glu Ala Pro Val
1               5                   10

<210> SEQ ID NO 26
<211> LENGTH: 13
<212> TYPE: PRT
<213> ORGANISM: Bos indicus

<400> SEQUENCE: 26

His Ala Gly Lys Tyr Ser Arg Glu Lys Asn Thr Ala Pro
1               5                   10

<210> SEQ ID NO 27
<211> LENGTH: 13
<212> TYPE: PRT
<213> ORGANISM: Bos indicus

<400> SEQUENCE: 27

His Ala Gly Lys Tyr Ser Arg Glu Lys Asn Thr Pro Ala
1               5                   10

<210> SEQ ID NO 28
<211> LENGTH: 14
<212> TYPE: PRT
<213> ORGANISM: Bos indicus

<400> SEQUENCE: 28

His Ala Gly Lys Tyr Ser Arg Glu Lys Asn Thr Pro Ala Pro
1               5                   10

<210> SEQ ID NO 29
<211> LENGTH: 8
<212> TYPE: PRT
<213> ORGANISM: Bos indicus

<400> SEQUENCE: 29

Ala His Ile Val Glu Arg Tyr Val
1               5

<210> SEQ ID NO 30
<211> LENGTH: 8
<212> TYPE: PRT
<213> ORGANISM: Bos indicus

<400> SEQUENCE: 30

Ala Ile Gln Val Glu Arg Tyr Val
1               5

<210> SEQ ID NO 31
<211> LENGTH: 9
<212> TYPE: PRT
<213> ORGANISM: Bos indicus

<400> SEQUENCE: 31

Ala His Ile Gln Val Glu Arg Tyr Val
1               5

<210> SEQ ID NO 32
<211> LENGTH: 15
<212> TYPE: PRT
<213> ORGANISM: Bos indicus
```

```
-continued

<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 32

Xaa Ala Leu Phe Gly Ala Gln Leu Gly Xaa Ala Leu Gly Pro Ile
1               5                   10                  15

<210> SEQ ID NO 33
<211> LENGTH: 8
<212> TYPE: PRT
<213> ORGANISM: Bos indicus

<400> SEQUENCE: 33

Lys Ala Ala Lys Pro Ser Val Pro
1               5
```